(12) United States Patent
Dapprich et al.

(10) Patent No.: US 9,103,827 B2
(45) Date of Patent: Aug. 11, 2015

(54) SEQUENCE-SPECIFIC EXTRACTION AND ANALYSIS OF DNA-BOUND PROTEINS

(75) Inventors: Johannes Dapprich, Lawrenceville, NJ (US); Benjamin Garcia, Princeton, NJ (US); Gary Leroy, Neptune, NJ (US)

(73) Assignees: The Trustees of Princeton University, Princeton, NJ (US); Generation Biotech, Lawrenceville, NJ (US)

( * ) Notice: Subject to any disclaimer, the term of this patent is extended or adjusted under 35 U.S.C. 154(b) by 102 days.

(21) Appl. No.: 13/884,716

(22) PCT Filed: Nov. 10, 2011

(86) PCT No.: PCT/US2011/060185
§ 371 (c)(1),
(2), (4) Date: Oct. 7, 2013

(87) PCT Pub. No.: WO2012/064954
PCT Pub. Date: May 18, 2012

(65) Prior Publication Data
US 2014/0024052 A1    Jan. 23, 2014

Related U.S. Application Data

(60) Provisional application No. 61/412,125, filed on Nov. 10, 2010.

(51) Int. Cl.
*G01N 33/53* (2006.01)
*G01N 33/566* (2006.01)
*G01N 33/68* (2006.01)

(52) U.S. Cl.
CPC .......... *G01N 33/566* (2013.01); *G01N 33/6842* (2013.01); *G01N 33/6875* (2013.01); *G01N 2440/00* (2013.01); *G01N 2500/02* (2013.01); *G01N 2570/00* (2013.01)

(58) Field of Classification Search
None
See application file for complete search history.

(56) References Cited

U.S. PATENT DOCUMENTS

| | | |
|---|---|---|
| 5,508,164 A | 4/1996 | Kausch et al. |
| 5,945,525 A | 8/1999 | Uematsu et al. |
| 2007/0099225 A1 | 5/2007 | Wilson et al. |
| 2009/0149337 A1 | 6/2009 | Hellyer et al. |

OTHER PUBLICATIONS

Vitharana, S. N. et al., "Fractionation of chromosome 15 with an affinity-based approach using magnetic beads", Genomics, 2006, vol. 87, pp. 158-164.

*Primary Examiner* — James Martinell
(74) *Attorney, Agent, or Firm* — Meagher Emanuel Laks Goldberg & Liao, LLP

(57) ABSTRACT

An automated protein preparation technology that may use magnetic microparticles to isolate proteins in their native state from specific genomic loci of interest via the chromatin to which they are bound is described. After extraction, the targeted proteins may be purified for downstream analysis by quantitative mass spectrometry or ELISA. The identification of DNA-bound proteins, histones and their post-translational modification is of high scientific and pharmaceutical importance due to the role of DNA-binding proteins in the cauzation and development of human disease; in particular, cancer.

30 Claims, 14 Drawing Sheets

```
In Lac operator segment:
256 copies of "AATTGTTATCCGCTCAC"              (17 bases)
224 copies of "AATTCCACATGTGGCCACA"            (19 bases)
 31 copies of "AATTCCACATGTGGAATTCCACA"        (23 bases)

In TetR segment:
 96 copies of "TCGAGTTTACCACTCCCTATCAGTGATAGAGAAAAGTGAAAG"   42 bases Thereafter unique CMV promoter sequence:    TCGTCGACCGGGTCGAGGTAG... etc.

5'-CTCGAGgaTCGACCTCGAGACTCTAGAGGCGCCGAATTCCACAATTGTTATCGCTCACAATTCCACATGTGGCC
ACAAATTGTTATCCGCTCACAATTCCACATGTGGCCACAAATTGTTATCGCTCACAATTCCACATGTGGCACAAATT
GTTATCCGCTCACAATTCCACATGTGGCCACAAATTGTTATCCGCTCACAATTCCACATGTGGCCACAAATTGTTATCC
GCTCACAATTCCACATGTGGCCACAAATTGTTATCCGCTCACAATTCCACATGTGGCCACAAATTGTTATCCGCTCACA
ATTCCACATGTGGAATTCCACATGTGGCCACAAATTGTTATCCGCTCACAATTCCACATGTGGCCACAATTCCACATG
TGGCCACAAATTGTTATCCGCTCACAATTCCACATGTGGCCACAAATTGTTATCCGCTCACAATTCCACATGTGGCCAC
A etc. ...       ...CTCACAATTCCACATGTGGAATTCCACATGTGGCCACAATTGTTATCCGCTCACAATGTGGCCACA
     31x   224x   256x
AATTGTTATCCGCTCACAATTCCACATGTGGCCACAAATTGTTATCGCTCACAATTCCACATGTGGCCACAAATTGTT
ATCCGCTCACAATTCCACATGTGGCCACAAATTGTTATCGCTCACAATTCCACATGTGGCCACAAATTGTTATCCGCT
CACAATTCCACATGTGGCCGAtccctcgagTTTACCACTCCCTATCAGTGATAGAGAAAAGTGAAAGTCGAGT
TTACCACTCCCTATCAGTGATAGAGAAAAGTGAAAGTCGAGTTTACCACTCCCTATCAGTGAT
CGAGTTTACCACTCCCTATCAGTGATAGAG etc.  ...   96x  ...TCGAGTTTACCACTCCCTATCA
GTGATAGAGAAAAGTGAAAGTCGAGTTTACCACTCCCTATCAGTGATAGAGAAAGTGAGTTTACCACTCCC
TATCAGTGATAGAGAAAAGTGAAAGTCGAGTTTACCACTCCCTATCAGTGATAGAGAAAAGTGAAAGTCGAGC
TGGTTTAGTGAACCGTCAGATCGCCTCTAGAGGCGTGGGAGGTAGCGTGTTTGACCTCCATAGAAGACCGATCC
AGCCTCCGCGGTGGCGGCCGCTCTAGACGGGCGACTAAAGGCCGAGGAGAGTCAGTTCAAGTACCACTCCC
GTGCCATCCTGGTCTGAGCGGACGACGTAAAACGGCCACAAGTTCAGTGTCCGGAGGGCGATCCA
CCTACGGCAAGCTGACCCTGAAGTTCATCTGCACCACCGGCAAGCT.. etc.  (~4kb) .. GCCCTTTCGTC-3'
```

Fig. 3

Figure 5. Example of a ChIP pulldown of the Protein Brd4 demonstrating proficiency in the isolation of histones sub-genome-wide. I is the Input, F flowthrough and E eluant from the ChIP.

Quantitative mass spectrometry analysis of histones from a ChIP-pulldown of Brd4 versus a control sample of genome-wide histones. Some histone post-translational modifications (PTMs) are overexpressed, underexpressed or not changing on the Brd4 histones when compared to the control.

High-throughput separation and MS characterization of modified combinatorial histone H3 forms. Mass spectra show that H3 forms with different PTMs are identified. ETD-MS/MS of the 9 methyl species reveals the sequence K14acK23acK27me3.

Fig. 8 Histone H3 residues 9-17 (K⁹STGGK¹⁴APR) Single Ion Chromatograph (Orbitrap MS¹)

SEQUENCE-SPECIFIC EXTRACTION AND ANALYSIS OF DNA-BOUND PROTEINS

CROSS-REFERENCE TO PRIOR FILED APPLICATION

This application claims priority to earlier filed PCT application PCT/US2011/060185 which was filed on Nov. 10, 2011 and U.S. provisional application 61/412,125 which was filed on Nov. 10, 2010 both of which are incorporated herein in their entirety.

SEQUENCE LISTING

The instant application contains a Sequence Listing which has been submitted in ASCII format via EFS-Web and is hereby incorporated by reference in its entirety. Said ASCII copy, created on Jul. 19, 2013, is named PRINCETON-15002_SL.txt and is 24,911 bytes in size.

FIELD OF INVENTION

The application relates to identification and analysis of DNA-binding proteins.

BACKGROUND

The regulation of DNA modification and translation through proteins binding to it is an important biological phenomenon. The identification of proteins bound to specific DNA loci is important to understand the regulation of biological function. Post-translational modification of nucleic acid binding proteins is an important biological phenomenon. Post-translational modification of histones is an important biological phenomenon.

SUMMARY

In an aspect, the invention relates to a method of isolating a nucleic acid binding protein. The method includes providing a sample that may contain a first nucleic acid molecule having a nucleic acid binding protein bound thereon, and providing a second nucleic acid molecule that has an affinity label. The second nucleic acid molecule is capable of binding to the first nucleic acid molecule to form a complex. The method also provides for selectively attaching an affinity label to the second nucleic acid molecule that targets a specific sequence or polymorphism based on a sequence- or SNP-dependent enzymatic extension of said second nucleic acid molecule. The method also includes isolating the complex through binding of the affinity label to a moiety capable of binding the affinity label, and obtaining the nucleic acid binding protein from the isolated complex. Alternatively peptides originating from the isolated nucleic acid binding protein can be obtained through a protein digest for subsequent analysis by methods such as mass spectrometry. Such protein digest can be performed directly on the isolated complex or alternatively on the nucleic acid binding protein after it has been obtained from the isolated complex.

In an aspect, the invention relates to a method of identifying a nucleic acid binding protein. The method includes providing a sample that may contain a first nucleic acid having a nucleic acid binding protein bound thereon, and providing a second nucleic acid that has an affinity label. The second nucleic acid is capable of binding to the first nucleic acid to form a complex. The method also include isolating the complex through binding of the affinity label to a moiety capable of binding the affinity label, and obtaining the nucleic acid binding protein from the isolated complex. The method also includes the identification of the DNA binding proteins. Such methods may include, but are not limited to, mass-spectrometry or antibody-based methods such as Western blots and ELISA assays.

In an aspect, the invention relates to a method of analyzing nucleic acid binding protein post-translational modification. The method includes providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and analyzing the nucleic acid binding protein.

In an aspect, the invention relates to a method of researching cancer at the molecular level. The method may include providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and analyzing the nucleic acid binding protein.

In an aspect, the invention relates to a method of researching human disease. The method may include providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and analyzing the nucleic acid binding protein.

In an aspect, the invention relates to a method of researching human disease, including but not limited to cancer. The method includes providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and identifying one or more of the nucleic acid binding proteins.

In an aspect, the invention relates to a method of assessing histone post-translational modification. The method may include providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and analyzing the nucleic acid binding protein.

In an aspect, the invention relates to a method of assessing epigenetic factors. The method may include providing a sample that may contain a first nucleic acid having a nucleic acid binding protein bound thereon, and providing a second nucleic acid that has an affinity label. The second nucleic acid is capable of binding to the first nucleic acid to form a complex. The method also includes isolating the complex through binding of the affinity label to a moiety capable of binding the affinity label, obtaining the nucleic acid binding protein from the isolated complex and analyzing the nucleic acid binding protein.

In an aspect, the invention relates to a method of screening drug candidates. The method includes providing a drug candidate to a sample, and providing a control substance to a control sample. The sample and the control sample may include a respective first nucleic acid that may have a respective nucleic acid binding protein. The method may include providing a second nucleic acid that has an affinity label. The second nucleic acid is capable of binding to the respective first nucleic acid in the sample and control sample to form a respective complex. The method also includes isolating the respective complexes through binding of the affinity label to a moiety capable of binding the affinity label, obtaining the respective nucleic acid binding proteins from the sample and control sample, and analyzing the respective nucleic acid binding proteins. The method may also include comparing the nucleic acid binding protein post-translational modification profile in the sample versus the control sample.

In an aspect, the invention relates to a method of identifying DNA binding proteins. The method includes selecting one or more samples taken from a cell line, a tumor cell line, a primary tissue cell line, a low passage tissue cell line, a xenograft, a tissue, a human tissue from a biopsy, a tissue from a preclinical species, a tissue from a disease model, any of above mentioned cell lines or tissues untreated or treated by any treatment such as for example a compound treatment. The sample or samples may include a first nucleic acid that may have a nucleic acid binding protein. The method includes providing a second nucleic acid that has an affinity label. The second nucleic acid is capable of binding to the first nucleic acid in the sample and control sample to form a respective complex. The method also includes isolating the respective complexes through binding of the affinity label to a moiety capable of binding the affinity label, obtaining the respective nucleic acid binding proteins from the sample and control sample, and identifying the respective nucleic acid binding proteins. The method also includes comparing the identified nucleic acid binding protein from the different samples if more than one sample is analysed. The method also includes comparing post-translational modification profiles of the proteins in one sample versus another sample.

In an aspect, the invention relates to a method of identifying regulatory proteins. The method includes identifying DNA binding proteins as previously described. The method also includes altering the activity of such DNA binding protein through methods that may include but are not limited to overexpression, mutation, knock-down, knock-out, chemical modification, inhibition, binding of an agonist, binding of an antagonist, altering the activity of a protein that is known or suspected to interact with the DNA binding protein. The method also includes observing the phenotype of the sample in which such modification was performed. The method also includes comparing the phenotype of the sample in which a modification was made to a control sample.

In an aspect, the invention relates to a method of identifying regulatory pathways. The method includes identifying DNA binding proteins as described previously. The method also includes identifying proteins that regulate the DNA binding of such DNA binding proteins through searches in the literature, or in pathway databases, or in knowledge databases. The method also includes altering the activity or level of such regulatory proteins, through treatment of selected samples by methods know in the art, including but not limited to treatment with a compound, knockdown by RNA interference, overexpression, or knockout. The method may include identifying the changes in DNA binding of the DNA binding proteins. The method may also include measuring the changes on mRNA expression levels as a response to such a treatment by transcriptomics or PCR-based methods. The method may also include assaying such cells for alteration in their phenotype.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 3 discloses the 'Lac operator' sequences as SEQ ID NOS 7-9, respectively, in order of appearance; the 'Tetr segment' as SEQ ID NO: 10; the 'CMV promoter sequence' as SEQ ID NO: 11 and the constructed full length sequence as SEQ ID NO: 12.

FIG. 7 discloses SEQ ID NO: 14.

FIG. 8 discloses SEQ ID NOS 2, 2-6 and 15-17, respectively, in order of appearance.

DETAILED DESCRIPTION OF THE PREFERRED EMBODIMENTS

Figure 1:
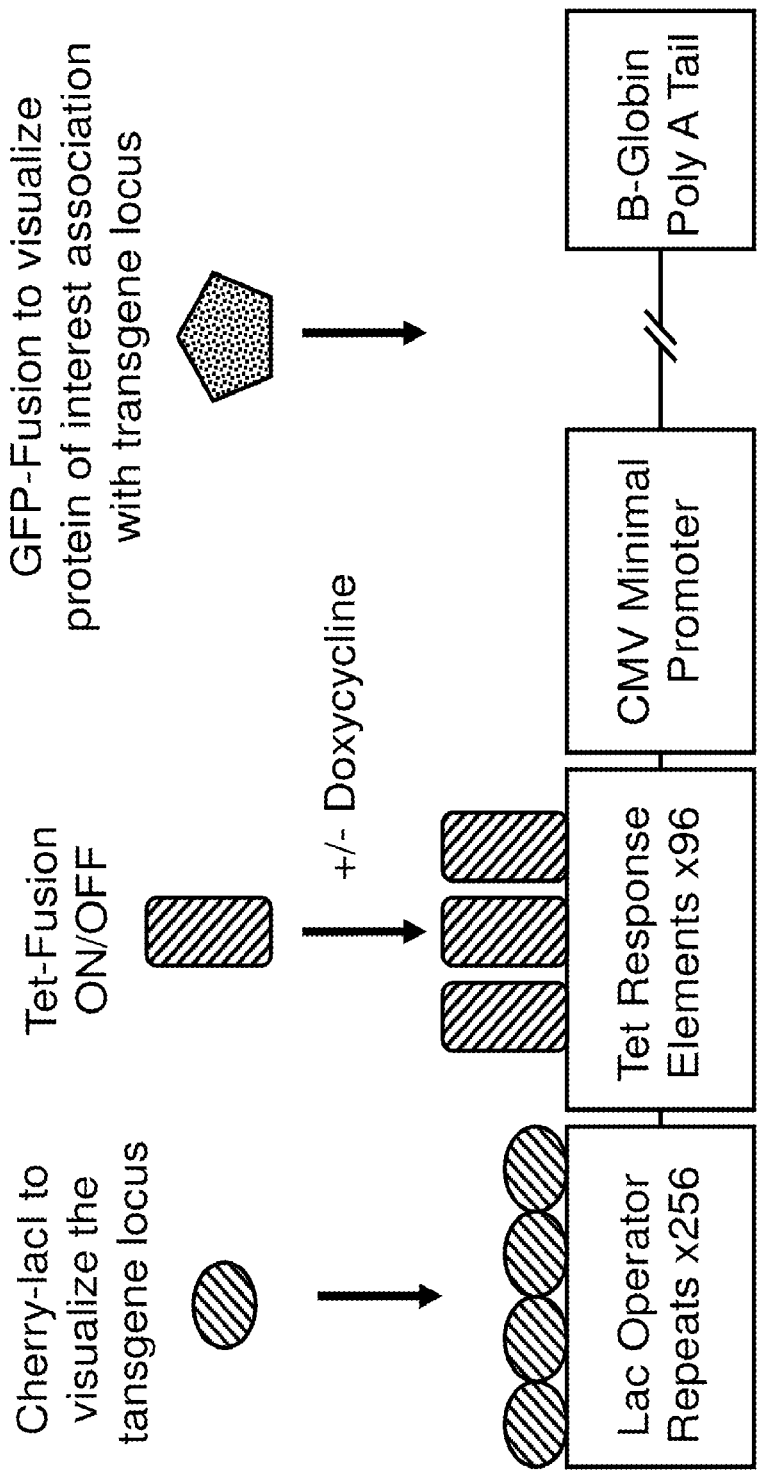
FIG. 1a illustrates a transgene model system.
FIG. 1b illustrates condensed versus open chromatin in a transgene model system.

Certain terminology is used in the following description for convenience only and is not limiting. The words "a," and "one," as used in the claims and in the corresponding portions of the specification, are defined as including one or more of the referenced item unless specifically stated otherwise. The phrase "at least one" followed by a list of two or more items, such as "A, B, or C," means any individual one of A, B or C as well as any combination thereof.

An embodiment provides an automated protein preparation technology that uses magnetic microparticles to isolate DNA-binding proteins in their native state from specific genomic loci of interest via the chromatin to which they are bound. After extraction, the targeted DNA-binding proteins may be purified.

In an alternative embodiment, further identification and/or analysis proceeds from unpurified complexes. For example, in one embodiment, the unpurified DNA-protein complexes may be subjected to a protease digest to obtain peptides for analysis by one or more methods of chromatography, mass spectroscopy (MS), high resolution MS, MS/MS, or antibody-based detection.

An embodiment provides for the identification of DNA-bound proteins analysis by mass spectrometry or ELISA or Western blot or other suitable methods known in the art.

An embodiment provides for the quantitative analysis of the DNA-bound proteins by mass spectrometry or ELISA or Western blot.

An embodiment provides for the analysis of DNA binding proteins and their post-translational modification.

An exemplary use of the identification and analysis of post-translational modification is the identification of histones and the analysis of their post-translational modification. Histones and their post-translational modification are of high scientific and pharmaceutical importance due to their role in the causation and development of human disease, in particular cancer. The technology herein will fill a distinct need in epigenomics and disease research and provide a new tool for the sequence- or SNP-specific candidate drug screening of potential histone deacetylase (HDAC) inhibitors. Prior to the present embodiments, no such ability existed.

A synthetic transgene was used to demonstrate and optimize an exemplary approach of targeting chromatin segments with sequence- or SNP-specific primers to recover attached specifically modified histones and other DNA-associated proteins in sufficient amounts to permit post-translational analysis. Further use was made of the fact that the nucleosome density of genomic chromatin is generally reduced for transcription factor binding sites. In conjunction with adjacent unique sequence elements, this provides convenient and highly relevant choices of target sites for primer-based capture of any specific locus. This generates high-resolution combinatorial histone code information for any disease-associated target region in a streamlined and largely automated process. The information gained can lead to the identification of target biomarkers and significantly improves currently available tools for protein detection, identification and quantification. The combined information of proteomic histone modification and of the underlying genomic sequence will contribute to a better understanding of cancer at the molecular level, as well as of other human diseases such as autoimmune and neurological disorders. The chromatin capture and mass spectrometry tools used for this purpose are both cutting edge and allow scaling up the technology to provide a highly sensitive and medium- to high-throughput analysis pipeline. One use may be identifying and characterizing histone modifications originating from specific disease-associated loci from tumor and normal biospecimens, such as the n-myc locus amplified in neuroblastoma. Based on the rapidly growing use of mass spectrometry, due to its versatility, sensitivity and throughput and the automation of the chromatin isolation procedure, sequence-specific protein extraction can be used in a clinical environment.

An exemplary use of the technology is based on chromatin prepared from neuroblastoma cell lines, or actual tumor versus normal samples of neuroblastoma.

Histone post-translational modifications (PTMs) are an intensely investigated field for improving human health. Alterations in these PTM patterns play distinct roles in the pathology of common diseases such as cancer, and the technology herein allows researchers and clinicians for the first time to correlate unique changes in the histone code to their underlying specific genomic sequence. This provides a comprehensive understanding of epigenetic signaling patterns at the molecular level and their role in the development and possible treatment of disease.

An embodiment provides an automated protein preparation technology that isolates DNA-bound proteins in their native state via the DNA in a sequence- or SNP-specific way and makes them available for downstream analysis by mass spectrometry or ELISA.

The identification of transcription factors, histones, and other proteins that bind to DNA is of particular interest because of their established high scientific and pharmaceutical importance in the causation and development of disease, in particular cancer, metabolic diseases, immune-related disease, and neurological diseases.

DNA-bound proteins may be isolated by adaption of a magnetic bead-based capture technology, haplotype- and region-specific extraction (HSE/RSE).

Current proteomics methods are limited by the ability to identify low abundance proteins among a preparation of proteins from a tissue or cell preparation. Even after enrichment for DNA binding proteins, it has been difficult or impossible to identify and analyze DNA-binding proteins among the background of other proteins that may bind non-specifically to DNA [Rusk, Nature Methods 6(3). 187, 2009]. Locus-specific isolation of DNA-bound proteins has been proposed and carried out with some success before. But current methods are typically limited in their efficiency, sensitivity and specificity, requiring large amount of input DNA-bound proteins for successful analysis [see Déjardin J, Kingston R E. Purification of proteins associated with specific genomic Loci. Cell. 2009 Jan. 9; 136(1):175-86 and references cited therein which are incorporated herein by reference as if fully set forth, as well as Mittler G, Butter F, Mann M. A SILAC-based DNA protein interaction screen that identifies candidate binding proteins to functional DNA elements. Genome Res. 2009 February; 19(2):284-93. Epub 2008 Nov. 17]. The current methods are not able to distinguish the targeted chromatin segments based on very small sequence variants, such as a SNP. The efficiency of DNA-bound protein capture from solubilized chromatin can be increased by cross-linking the proteins to their specific targeted carrier DNA regions prior to extraction through formaldehyde treatment and subsequent reversal after extraction through exposure to a mercaptoethanol solution [see ibid—Déjardin et al.].

The capture efficiency and specificity of DNA-targeting primers can be increased by various means. Selecting unique target sequences near a known transcription factor binding site is advantageous because that sequence is generally expected to be more readily accessible for targeting. The combination of tightly binding and 3'-extendable primers is advantageous because it provides a means to target specific sequences under relatively gentle denaturation conditions. Examples for more tightly binding but 3'-extendable targeting primers are oligonucleotides that are comprised of partially or fully locked nucleic acid (LNA) or peptide nucleic acid (PNA) residues at or near their 5'-end as well as of extendable DNA residues at their 3'-end. The targeting element can alternatively be a polypeptide, a polypeptide complex or an oligonucleotide-polypeptide complex that binds specifically to a target sequence. Examples of such targeting elements include, e.g., a restriction enzyme, a transcription factor, RecA, nuclease, and a sequence-specific DNA-binding protein. The targeting element can alternatively, or in addition, be a hybrid, complex or tethered combination of one or more of these targeting elements.

Allelic discrimination based on SNPs or other polymorphisms is possible with the use of proof-reading enzymes such as Phi29 in isothermal assays. In this case the oligonucleotide primers are enzymatically 3'-extendable but protected from exonucleolytic digestion through an appropriate 3'-modification, such as through two thiophosphate linkages at the 3' terminus. This embodiment is advantageous in combination with alkaline or low-temperature denaturation conditions that reduce DNA fragmentation and disruption of chromatin. The ability to carry out enzymatic discrimination between different alleles through the use of polymorphic sites in an isothermal assay can be particularly valuable because of the relative simplicity and automatability of the procedure. The discrimination depending on the identity of individual SNPs therefore allows the ability to link data from SNP-based genome-wide association studies (GWAS) with the proteins binding at a specific allele.

The embodiment described herein provides for a selective isolation of proteins bound to a specifically targeted DNA region, gene, pseudogene, homologue, allele or haplotype. In a preferred embodiment, biotin-modified nucleotides are used for the enzymatic incorporation step, but a number of other haptens and nucleotide modifications are known to be compatible with enzymatic incorporation as well. It is in particular possible to use modified nucleotides with haptens on extended spacers or linker molecules in enzymatic assays so that better steric accessibility of the attached hapten for subsequent capture by magnetic particles is achieved [see ibid—Déjardin et al.].

Elution of the biotin attached to streptavidin can reversibly be achieved in low salt conditions [Holmberg A, Blomstergren A, Nord O, Lukacs M, Lundeberg J, Uhlén M.; The biotin-streptavidin interaction can be reversibly broken using water at elevated temperatures, Electrophoresis. 2005 February; 26(3):501-10] or through other means such as the use of desthiobiotin [Hirsch J D, Eslamizar L, Filanoski B J, Malekzadeh N, Haugland R P, Beechem J M, Haugland R P.; Easily reversible desthiobiotin binding to streptavidin, avidin, and other biotin-binding proteins: uses for protein labeling, detection, and isolation; Anal Biochem. 2002 Sep. 15; 308(2):343-57].

The sequence-specific isolation of large DNA segments and DNA-bound proteins can be achieved with single capture primers. If desired, the chromatin can be sheared before extraction to achieve smaller capture sizes, thereby providing less protein material per capture primer for analysis but an increased resolution per targeted DNA sequence. Typical fragment lengths of DNA that can be captured by a single primer using HSE/RSE are 1 kb, 2 kb, 5 kb, 10 kb, 15 kb, 20 kb, 25 kb, 30 kb, 35 kb, 40 kb and 50 kb; with some embodiments allowing the capture of DNA segments of 100-250 kb length. The likelihood of DNA cross-hybridization causing unspecific background from non-targeted material increases when capturing large DNA segments. This can be reduced through the use of Cot-1 DNA that saturates the common repeat elements in the targeted fragments which constitute the most likely regions for cross-hybridization. The targeted capture of both the underlying genomic DNA and the DNA-bound proteins associated with it allows the combined analysis of epigenetic or other modifications that occur on the DNA itself (such as methylation or various types of DNA damage) as well as modifications that occur on the DNA-bound proteins (such as histone code). An embodiment provides a method to 1) recover proteins bound to the region targeted by haplotype- and region-specific extraction (HSE/RSE) and 2) identify such proteins—including their chemical modifications—using one or more of chromatography, mass spectroscopy, high resolution MS, MS/MS, antibody detection.

Embodiments herein provide 1) the targeting of potentially large genomic DNA segments in a locus- or SNP-specific manner, and 2) the efficient recovery of native chromatin and subsequent release of attached histones in sufficient amounts to permit post-translational analysis. The combination results in a DNA preparation and mass spectrometry analysis platform that can generate high-resolution combinatorial information of the histone code for disease-associated genomic target regions in a streamlined and largely automated process.

In an embodiment, a stand-alone sample preparation platform that mirrors existing HAPLOPREP™ and SNPSEQ applications of the HSE/RSE technology is provided.

Examples of embodiments herein will demonstrate reliable preparation of a plasmid transgene such that it contains specific (and different) histone modifications on identical underlying DNA sequences. Examples of embodiments herein will demonstrate sequence-specific isolation and analysis of post translational histone modifications. Particular preparations of the histone-loaded genomic DNA as prepared above are targeted with extraction primers that are designed to be specific for elements of the underlying transgene sequence. After extraction, the DNA-bound co-precipitated histones is released from the targeted chromatin and purified for analysis by high-end combinatorial mass spectrometry. By these examples, it will be shown that 1) proteins such as histones and their modifications can successfully be detected, indicating sufficient sensitivity, and that 2) at least a majority of such modifications correspond to the appropriate histone state prepared, thereby indicating sequence specificity of downstream mass spectrometry. As a second assay to ensure sequence specificity, realtime PCR and sequencing can be used to determine relative copy numbers for the targeted transgene locus versus for a non-targeted control DNA. This combination (protein-based MS and DNA-based RT-PCR/seq) provides a clear picture of the experimental outcome for each protocol, which in turn allows the iterative optimization of the procedure for each targeted locus or allele.

An embodiment provides a robotic platform for methods herein. Methods herein may be implemented with the BioExtract2, EZ1 Biorobot™, or BioSprint96™

An example of the technology may be provided by targeting the n-myc variable copy number region that is strongly associated with neuroblastoma, using chromatin prepared from the IMR-32, CHP-126 or -212 cell lines from ATCC. Examples may also apply the technology to actual tumor versus normal samples of neuroblastoma.

The ability to reliably characterize histones in their native state after pulling them out in a locus-specific manner could revolutionize the study of post-translational modifications (PTMs) of disease-related genes.

The Histone Code hypothesis states that single modifications on histones are established and maintained in distinct genomic regions and form a binding platform that will recruit protein machinery leading to exclusive downstream functions such as activation or repression of target genes. These modifications on histones can be affected by both internal and environmental factors and are passed on from cell generation to generation, epigenetically. Histone PTM-mediated epigenetic mechanisms have shown to play extraordinary roles in human biology and human diseases such as cancer as well as autoimmune and neurological disorders. For example, misdirected targeting of histone acetyltransferases (HATs) and histone deacetylases (HDACs) occur in several types of leukemia. The epigenetics departments of nearly every major pharmaceutical company have a keen interest in the screening of potential HDAC inhibitors because of these enzymes' high potential value as key targets for successful new cancer drugs. Small molecule HDAC inhibitors are currently in various phases of clinical trials for treating several forms of cancer. Nevertheless, the precise epigenetic mechanisms underlying these diseases are not currently fully understood. Example for current efforts in this field on the scale of the Human Genome Project are The International Human Epigenome Project, the Alliance for the Human Epigenome and Disease (AHEAD), the Epigenome Network of Excellence, and others. Understanding epigenetic changes in a sequence-specific manner would not only immediately impact human disease research but also have far-reaching implications in other fields, such as agriculture and stem cells.

Embodiments herein provide methods to isolate and characterize proteins (e.g., histones) from a complex mixture in a locus- or SNP-specific way. This is beyond the limits of all current known technologies. Most histone-related research work is centered on the use of antibodies that recognize a single histone PTM (Western blot, immunofluorescence, chromatin immunoprecipitation: ChIP, etc.) for detection and isolation of any associated DNA sequence. However, experiments using histone site-specific antibodies are not known to allow DNA-based locus-specific targeting. Recently, mass spectrometry (MS) has become a complementary unbiased technique for chromatin research with its rapid nature and accuracy in assigning or also uncovering novel histone PTMs. See, for example, Trelle, M. B.; Jensen, O. N., Functional proteomics in histone research and epigenetics. Expert Rev Proteomics 2007, 4, (4), 491-503; and Garcia, B. A., Mass spectrometric analysis of histone variants and post-translational modifications. Front Biosci (Schol Ed) 2009, 1, 142-53, which are incorporated herein by reference as if fully set forth.

Since most MS strategies digest histone proteins into small peptides (="Bottom Up MS"), it becomes difficult to determine which histone peptides were created from the same protein molecule and information concerning the combinatorial nature of PTMs is difficult to recover. In an embodiment, methods herein employ a different strategy to sequence intact proteins (="Top Down MS"). See, for example, Kelleher, N. L., Top-down proteomics. Anal Chem 2004, 76, (11), 197A-203A; and Young, N. L.; Plazas-Mayorca, M. D.; Garcia, B. A., Systems-wide proteomic characterization of combinatorial post-translational modification patterns. Expert Rev Proteomics 7, (1), 79-92, which are incorporated herein by reference as if fully set forth. By merging front-end DNA extraction technology described herein with downstream combinatorial mass spectrometry analysis, the technology herein allows for the first time the ability to study histone modifications on chromatin segments of interest in a sequence-specific and largely automated way.

Two abilities need to be combined in order to enable the technology include: 1) Sequence-specific sample preparation and 2) highly sensitive downstream analysis of histones.

In an embodiment, chromatin isolation is achieved by a variation of haplotype- and region-specific extraction (HSE/RSE). HSE/RSE is an automated, magnetic bead-based capture technology used for tissue typing, forensics, breakpoint mapping and translocation analysis, and the selective isolation of candidate regions from genomic DNA or mixed samples, such as tumor vs. normal. HSE/RSE may utilize sequence- or SNP-specific capture primers that are enzymatically extended with biotinylated nucleotides after binding to their target sites. HSE/RSE may be multiplexed, adapted to any set of genes or regions of interest and allows the reliable isolation of original template DNA based on a single capture point without amplification. See, for example, Dapprich J, Cleary M A, Gabel H W, Akkapeddi A, Iglehart B, Turino C, Beaudet L, Lian J, Murphy N B. A Rapid, Automatable Method For Molecular Haplotyping. HLA 2004: Immunobiology of the Human MHC. Proceedings of the 13th International Histocompatibility Workshop and Congress. (Hansen J A and Dupont B, eds), Volume I & II, IHWG Press, Seattle, Wash., 2004. ISBN: 0-945278-03-9; Nagy M, Entz P, Otremba P, Schoenemann C, Murphy N, Dapprich J Haplotype-specific extraction: a universal method to resolve ambiguous genotypes and detect new alleles—demonstrated on HLA-B. Tissue Antigens. 2007 February; 69(2):176-80. PMID: 17257321; and Dapprich J, Ferriola D, Magira E E, Kunkel M, Monos D. SNP-specific extraction of haplotype-resolved targeted genomic regions. Nucleic Acids Res. 2008 Jul. 8. PMID: 18611953, which are incorporated herein by reference as if fully set forth. One advantage over other technologies is that even large chromosomal segments are enriched with high efficiency.

In an example of chromatin isolation herein, 600 ng of genomic DNA was found to provide about $3 \times 10^9$ histones after a single extraction. Compared to the lower MS detection limit, $6 \times 10^5$ histones (~$10^{-18}$ moles), this is 1000× more than required for the method. By this level of isolation, multiple analyses per sample may be enabled, as well as locus-based fine-mapping through shearing or enzymatically cutting the chromatin before extraction. In this way, information on the histone states may be obtained at a higher resolution. A similar approach may be found in Gabriel A, Dapprich J, Kunkel M, Gresham D, Pratt S C, Dunham M J. Global mapping of transposon location. PLoS Genet. 2006 Dec. 15; 2(12):e212. Epub 2006 Nov. 1. PMID: 17173485, which is incorporated herein by reference as if fully set forth.

Any single embodiment herein may be supplemented with one or more element from any one or more other embodiment herein.

EXAMPLES

The following non-limiting examples are provided to illustrate particular embodiments. The embodiments throughout may be supplemented with one or more detail from any one or more example below.

Example 1

An exemplary synthetic transgene model system was developed. See Janicki S M, Tsukamoto T, Salghetti S E, Tansey W P, Sachidanandam R, Prasanth K V, Ried T, Shav-Tal Y, Bertrand E, Singer R H, Spector D L. From silencing to gene expression: real-time analysis in single cells. Cell. 2004 Mar. 5; 116(5):683-98, which is incorporated herein as if fully set forth. Referring to FIG. 1a, the synthetic transgene model system contains 200 copies per cell of a stably integrated transgene located in a condensed, transcriptionally inactive (heterochromatic) region of chromosome 1 which provides several convenient layers of regulation. Each transgene has 256 copies of the lac operator sequence at the 5' end of the construct, which allows visualization of the integrated transgene upon binding of a Cherry-lac fusion protein. Downstream of the lac element are 96 copies of the tetracycline response element followed by a minimal CMV promoter. When the synthetic transcriptional activator TetON-VP16 is produced in presence of doxycycline, it activates transcription of the transgene from the minimal CMV promoter.

Referring to FIG. 1b, prior to induction of transcription by the TetON-VP16 fusion protein, the chromatin containing the transgene array is heavily trimethylated chromodomain HP1 proteins and condensed when visualized by confocal microscopy (≈0.9 μm in diameter; FIG. 1b, on left), i.e. a gene in a silenced state. Upon induction of transcription, the locus containing the transgene array becomes decondensed (≈2.0-4.5 μm diameter; FIG. 1b, on right), depleted of histone H3 lysine 9 trimethylation, which is concurrent with heterochromatic HP1 proteins leaving the locus—all characteristics of an active gene. Within two hours of the induction of the locus, the transgene chromatin becomes hyperacetylated and is directly bound by the euchromatic bromodomain (Brd) proteins. Moreover, these proteins are completely absent from the locus prior to induction. Such changes in histone code at the locus are directly visible through immunofluorescent staining with a histone PTM-specific antibody. An advantage of this system is that changes in chromatin structure and the localization of proteins can not only be very well controlled through the tetracycline transactivator ON/OFF status, but also examined in real time via chromatin decondensation and the binding of GFP-tagged chromatin associated proteins.

Example 2

Figure 2:
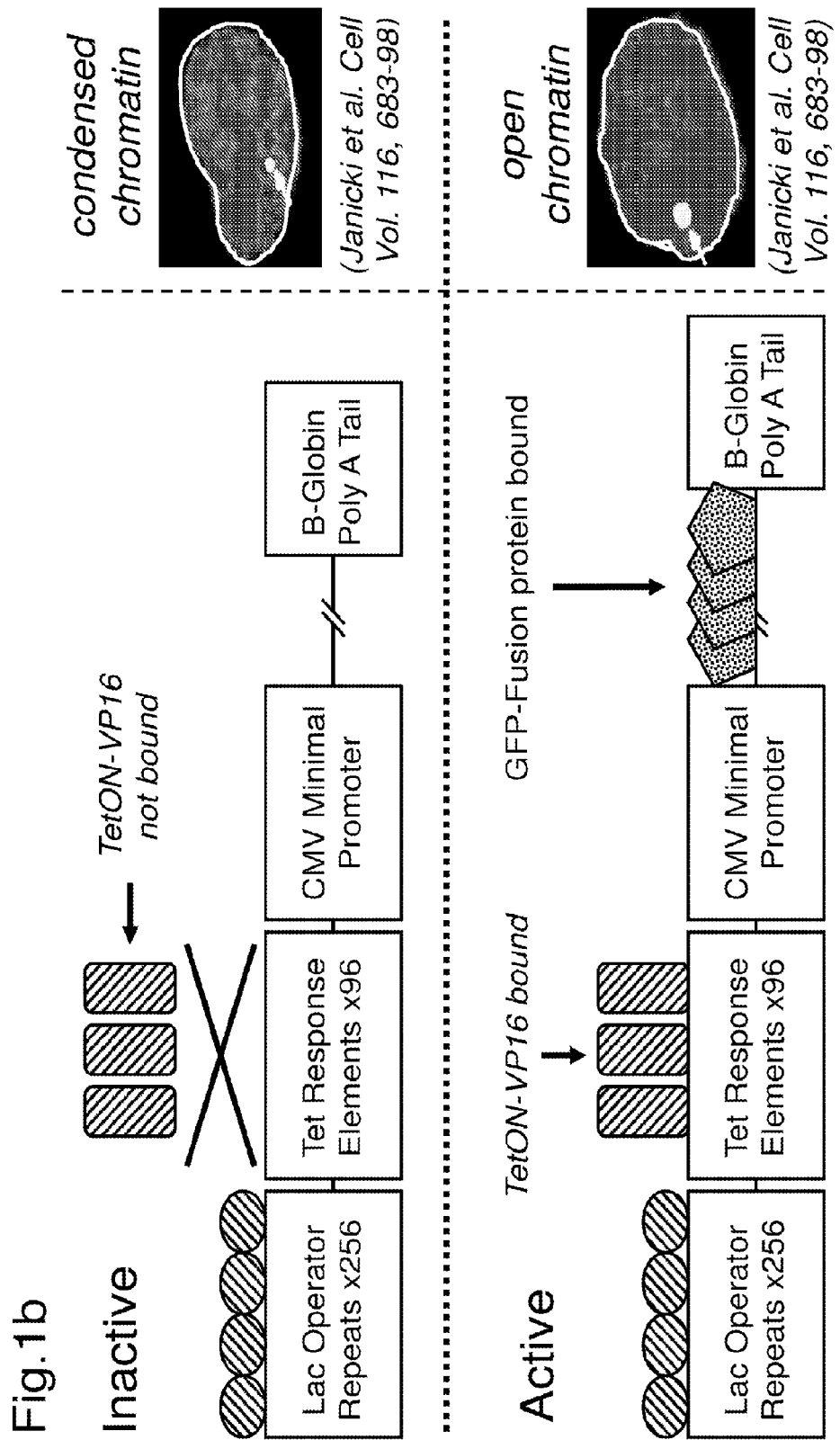
FIG. 2a illustrates a chromatin containing the transgene.
FIG. 2b illustrates released transgene chromatin fragments (about 200 per cell).
FIG. 2c illustrates addition of sequence-specific primers to transgene chromatin fragments and extension, and isolation of histones.
FIG. 2d illustrates histones that are separated from the isolated chromatin by acid wash for analysis.

Targeting of the transgene chromatin with sequence-specific primers. Referring to FIG. 2, DNA-associated histones are targeted and retained with high efficiency in step c) of FIG. 2. Three primary steps may be addressed to this end: 1) Sequence-specific capture primers are placed into double-stranded genomic DNA while keeping the associated chromatin structure of neighboring areas largely intact. 2) The hybridized primers are enzymatically extended with sufficient efficiency and distance to allow incorporation of biotinylated nucleotides. 3) The tagged chromatin segments are magnetically captured with sufficient specificity, efficiency and distance to allow the purification of DNA-bound histones for analysis by mass spectrometry. In an example, these steps are accomplished by the following: Nuclei are first isolated from cells in which the transgene array has been un-induced (condensed=OFF) or induced (open=ON) through the TetON transactivator (FIG. 2a). The chromatin containing the transgenes is then digested by cleavage with a restriction enzyme, in this example MSC-1 (due to its construction, each of the 256 lacI binding sites in each transgene contains an MSC-1 site). The nuclei are pelleted into a slurry and lysed, releasing the targeted transgene chromatin fragments (about 200 per cell) into the supernatant (FIG. 2b). Sequence-specific primers are added to the purified supernatant, hybridized to their target sequence and enzymatically extended with a mixture of regular and biotinylated nucleotides (diagonal arrows in FIG. 2c), thereby tagging the chromatin segments of interest for extraction. The sample is then incubated with streptavidin-coated magnetic microparticles to bind and purify the transgene chromatin (FIG. 2c). In a step, the histones are separated from the isolated chromatin by acid wash (which may not affect the histone code in any way) for analysis by mass spectrometry (FIG. 2d). The purity of the isolate may be monitored and blocking buffer and magnetic bead surface may be modified as necessary to reduce or eliminate unspecific pull-down of histones that might occur through unspecific binding.

Figure 3:
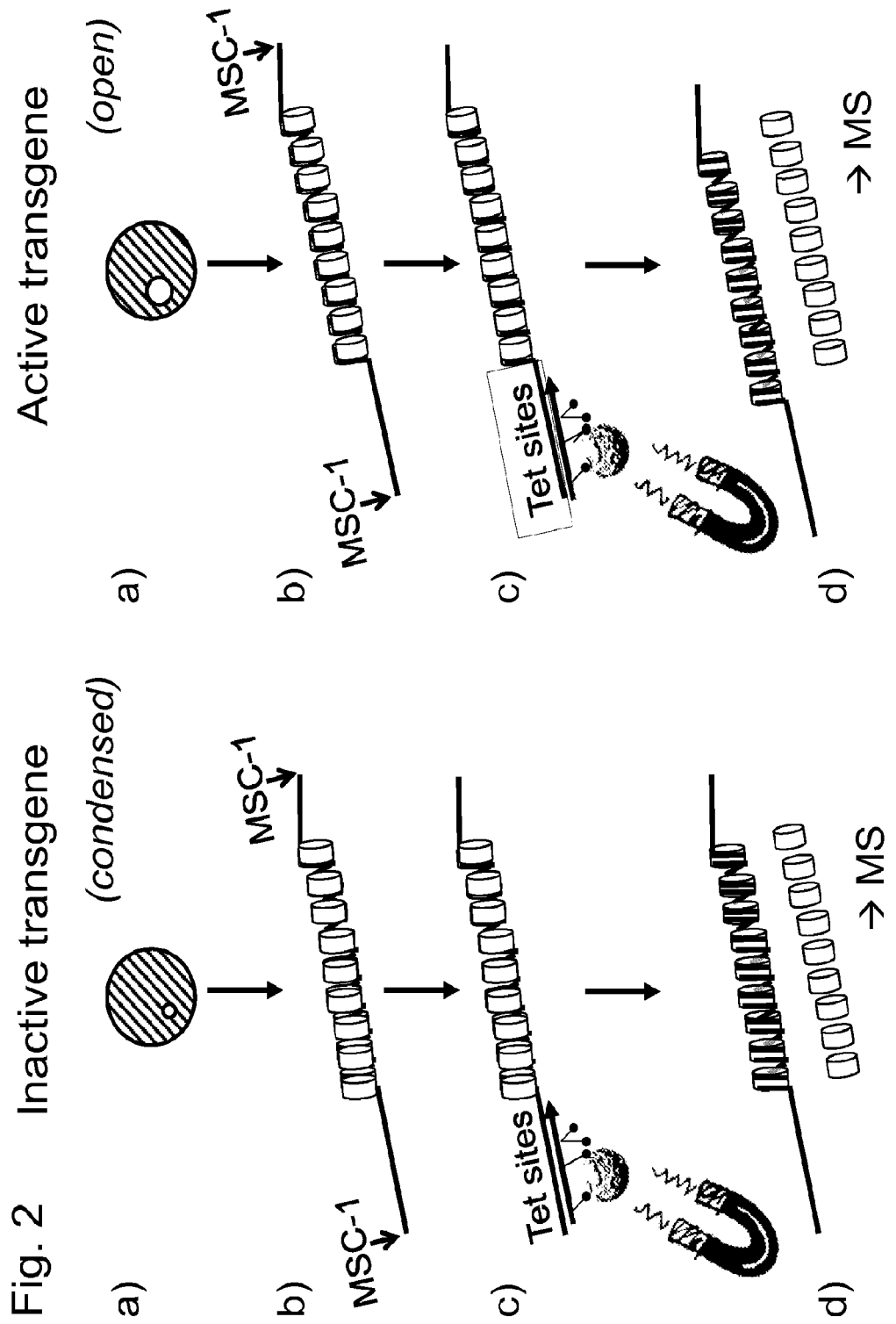
FIG. 3 illustrates features of a transgene model system.

The transgene chromatin may be further enriched by choosing to not lyse the nuclei and instead relying on the MSC-1-excised fragments to escape into the supernatant through the nuclear pores by diffusion. MSC-1 is a 6 base pair cutter and the sequence it cuts will occur randomly only approximately every 40,000 base pairs. Such large fragments of genomic DNA tend to remain trapped in unlysed nuclei and can thus easily be removed. By controlling the approximate number of cuts through varying the MSC-1 enzyme concentration and incubation time, fragments can be created with portions of uncut MSC-1 sequence at the 5'-end of the target locus that serve as additional capture point options. For the targeting step, the following features may be utilized: each transgene contains 256 lacI binding sites with three distinct sequences that are each repeated 256, 224 and 31 times (FIG. 3, sequence block on top in green, blue and yellow) and a TetON/OFF controlled promoter with 96 Tetr binding sites (center of FIG. 3, yellow). These repeat sequences are between 17-42 bases in length. Together with the unique transcription cassette (FIG. 3, sequence in red, unhighlighted), this provides a choice of multiplexed and singular capture points for the 5.5 kb targeted chromatin segment on which the extraction conditions can be optimized to achieve maximum overall efficiency and specificity.

Example 3

High-efficiency chromatin isolation. Successful design of capture primers for applications using plasmid and genomic DNA from a variety of sources may be utilized as a model. See, for example, Gabriel A, Dapprich J, Kunkel M, Gresham D, Pratt S C, Dunham M J. Global mapping of transposon location. PLoS Genet. 2006 Dec. 15; 2(12):e212. Epub 2006 Nov. 1. PMID: 17173485; Gupta T, Marlow F L, Ferriola D, Mackiewicz K, Dapprich J, et al. (2010) Microtubule Actin Crosslinking Factor 1 Regulates the Balbiani Body and Animal-Vegetal Polarity of the Zebrafish Oocyte. PLoS Genet 6(8): e1001073. doi:10.1371/journal.pgen.1001073; Dapprich J, Magira E, Samonte M A, Rosenman K, Monos D. Identification of a novel HLA-DPB1 allele (DPB1*1902) by haplotype-specific extraction and nucleotide sequencing. Tissue Antigens. 2007 March; 69(3):282-4. PMID: 17493157; Dapprich J, Witter K, Gabel H W, Murphy N B, Albert E D. Identification of a new HLA-B allele (B*1576) by haplotype specific extraction. Hum Immunol. 2007 May; 68(5):418-21. Epub 2007 Feb. 15. PMID:17462508; Dapprich J. Single-molecule DNA digestion by lambda-exonuclease. Cytometry. 1999 Jul. 1; 36(3):163-8. PMID: 10404963; Dapprich J, Nicklaus N. DNA Attachment to Optically Trapped Beads in Microstructures Monitored by Bead-Displacement. Bioimaging, 1998 March, 6 (1):25-32; Preuss R, Dapprich J, Walter N G. Probing RNA-protein interactions using pyrene-labeled oligodeoxynucleotides: Qbeta replicase efficiently binds small RNAs by recognizing pyrimidine residues. J Mol Biol. 1997 Oct. 31; 273(3):600-13. PMID: 9356249; Widengren J, Dapprich J, Rigler R. Dye-Nucleotide Interactions Investigated by Use of Fluorescence Correlation Spectroscopy. Chem. Phys., 1997 April 216:417-426; and Dapprich J, Walter N G, Salingue F, Staerk H. Base-dependent Pyrene Fluorescence used for In-Solution Detection of Nucleic Acids .J. of Fluorescence, Supplement, 1997 Mar. 7 (1):875-89S, which are incorporated herein by reference as if fully set forth.

Figure 4:
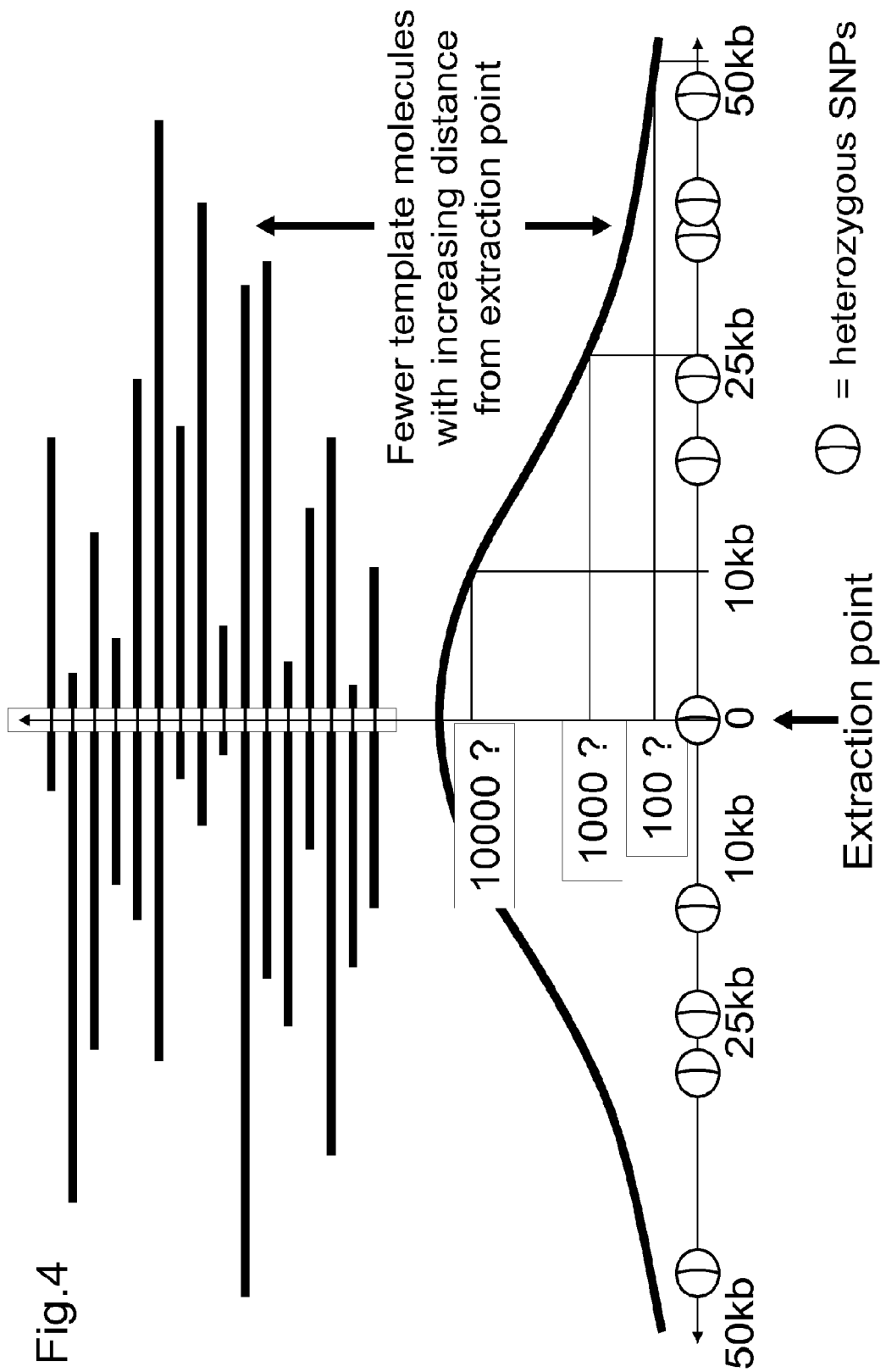
FIG. 4 illustrates that active magnetic mixing protocols used on HSE/RSE robots facilitate highly efficient (37%) capture of even very large targeted chromosomal segments.

Referring to FIG. 4, a unique active magnetic mixing protocol used on HSE/RSE robots facilitate highly efficient (37%) capture of even very large targeted chromosomal segments (FIG. 4). Embodiments herein target the genomic DNA itself, instead of specific proteins that may be associated with a particular sequence. For an application with similar conditions, all retrotransposon insertion points in two strains of yeast were targeted and then compared them by DNA microarray analysis. See, for example, Gabriel A, Dapprich J, Kunkel M, Gresham D, Pratt S C, Dunham M J. Global mapping of transposon location. PLoS Genet. 2006 Dec. 15; 2(12):e212. Epub 2006 Nov. 1. PMID: 17173485, which is incorporated herein by reference as if fully set forth. No amplification of the captured material was required before microarray detection. In another study, it was determined that the efficiency of DNA capture is directly compatible with the input requirements for tailing and sequencing of a next-generation sequencing platform, thus making amplification unnecessary.

Example 4

Optimization of isolation protocol. Primers designed in both forward (towards the center of the targeted gene) and reverse orientation can be utilized to test the required minimum distance for successful extension and biotinylation, as well as the ability for specific polymerases to continue extension into regions that are potentially highly occupied by nucleosomes and other proteins. Optimization can be achieved by testing with 'Regular' Taq polymerase versus the strand-displacing Phi29 polymerase for this purpose, and the concentration of capture primers, enzyme and other relevant reaction components (i.e. Na+, Mg2+) are varied along with denaturation and hybridization conditions to achieve gentle but efficient chromatin targeting and capture. All extracted material may be used in single mass spectrometry experiments. Fractions of each isolate may be used in single mass spectrometry experiments in order to test the feasibility of running multiple and replicate analyses. Example 5—N-myc locus in neuroblastoma.

Extraction of histones of the neuroblastoma-related N-myc locus from DNA prepared from the IMR-32 and CHP-126 or -212 cell lines. These cell lines contain high (120) copy numbers and abnormal histone code and expression of the N-myc locus on chromosome 2, which is a typical feature of this usually fatal pediatric cancer. It is not known why and how this amplification first occurs in patients, and a method herein may be able to help explain its origins and downstream effects. With carefully prepared DNA, it is possible to isolate segments of about 50 kb average size. See, for example, Nagy M, Entz P, Otremba P, Schoenemann C, Murphy N, Dapprich J Haplotype-specific extraction: a universal method to resolve ambiguous genotypes and detect new alleles—demonstrated on HLA-B. Tissue Antigens. 2007 February; 69(2):176-80. PMID: 17257321; and Dapprich J, Ferriola D, Magira E E, Kunkel M, Monos D. SNP-specific extraction of haplotype-resolved targeted genomic regions. Nucleic Acids Res. 2008 Jul. 8. PMID: 18611953, which are incorporated herein by reference as if fully set forth. This allows pulling down on the order of 100.000 histones on a single chromatin fragment.

Example 6

Mass Spectrometry of Isolated Histones

The sequence-based Histone Code of the purified chromatin is identified by high-end mass spectrometry.

Figure 5:
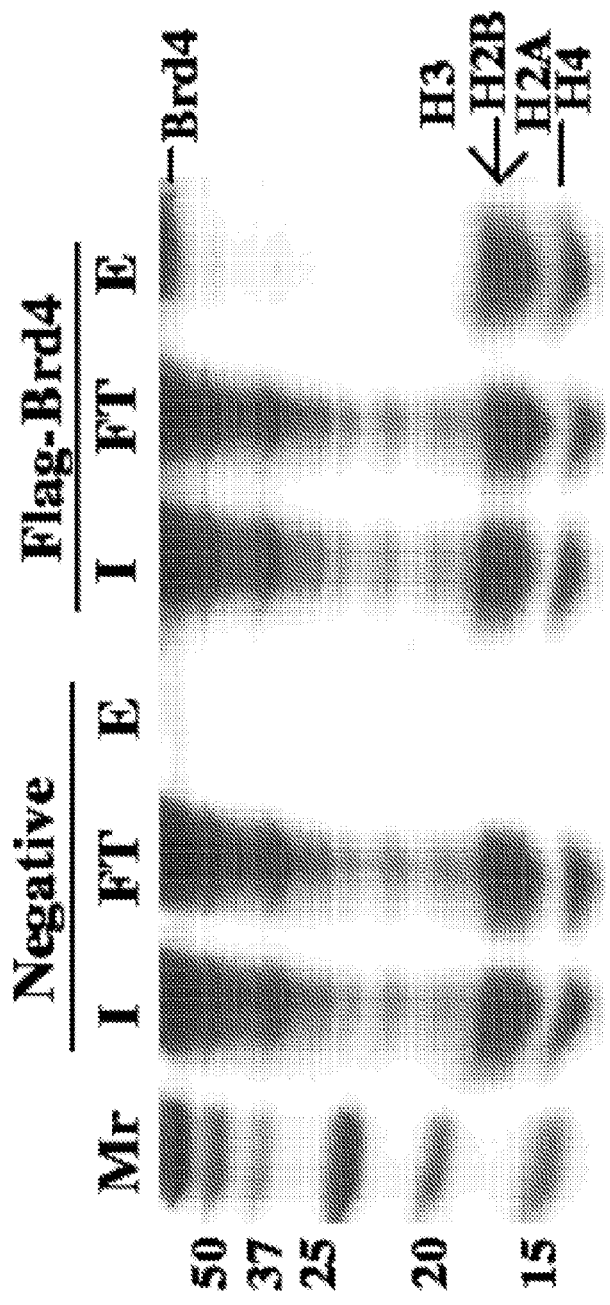
FIG. 5 illustrates ChIP pulldown.

Mass spectrometry (MS) has become a powerful tool for histone post-translational modification (PTM) analysis. See, for example, Garcia, B A, Mass spectrometric analysis of histone variants and post-translational modifications. Front Biosci (Schol Ed) 2009, 1, 142-53, which is incorporated herein as if fully set forth. Most MS analyses of histone PTMs/variants have been performed in a non-quantitative manner, some labeled and non-labeled approaches have been limitedly used. However, nearly all reports are very low throughput and involve extensive offline fractionation of histones in order to reduce sample complexity (separation of family members or modified forms). Therefore, quantitative, robust, high-sensitivity methods for interrogating both single and combinatorial Histone Codes are provided. This is currently not available otherwise by any other means and matches the sequence-specific extraction perfectly. Referring to FIG. 5, an approach was developed that rapidly identifies and quantifies histone variants and PTMs with comparable sensitivity but much higher throughput than standard MS approaches from ('regular') chromatin immunoprecipitated (ChIP) material. See, for example, Plazas-Mayorca, M. D.; Zee, B. M.; Young, N. L.; Fingerman, I. M.; LeRoy, G.; Briggs, S. D.; Garcia, B. A., One-pot shotgun quantitative mass spectrometry characterization of histones. J Proteome Res 2009, 8, (11), 5367-74; and LeRoy, G.; Rickards, B.; Flint, S. J. The double bromodomain proteins Brd2 and Brd3 couple histone acetylation to transcription. Mol Cell 2008, 30, (1), 51-60, which are incorporated herein as if fully set forth. The isotopic labeling of samples may be centered on the derivatization of histogenerated peptides with the reagent propionic anhydride that were obtained with varying amounts of deuterium atoms. The protocol allows for the highly sensitive quantification of all histone variants (with most PTMs) by high resolution MS, which may allow for direct multiplexed comparison of 2-3 samples in a single 1½ hour analysis from minute sample quantities ($\sim 10^{-18}$ moles).

The example above represents an ideal condition to accomplish a 'reverse ChIP' approach as herein described.

Example 7

Combinatorial Histone Codes

Figure 6:
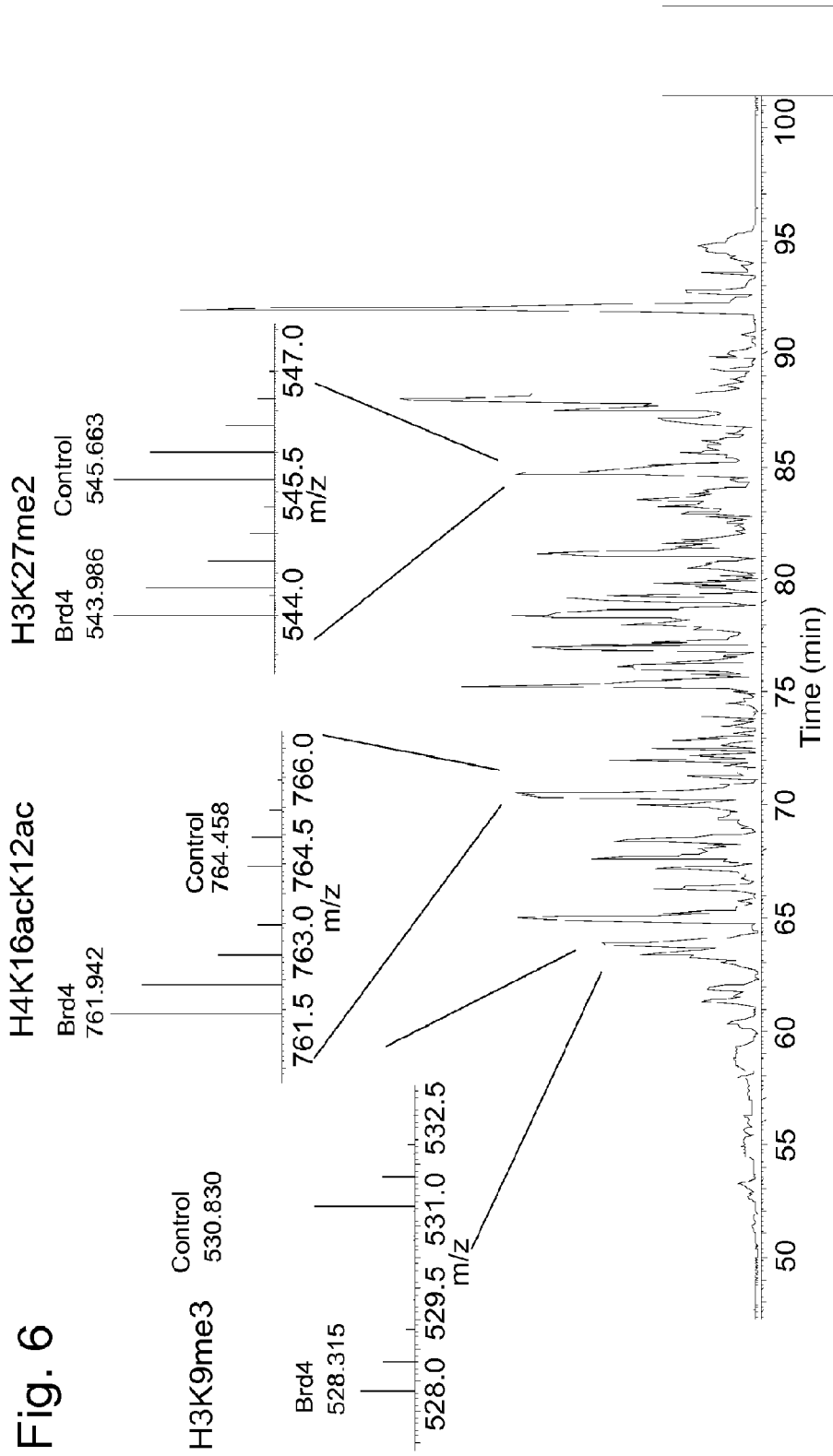
FIG. 6 illustrates quantitative mass spectrometry analysis of histones from a ChIP-pulldown.

The methodology has been extended to quantify the combinatorial Histone Codes. Histone Codes means the histone equivalent of DNA 'haplotypes', which may be vastly more informative than singular modifications (e.g., DNA 'SNPs'). Referring to FIG. 6, an example is provided where native ChIP (i.e., 'regular' ChIP) was performed against selected Histone Code Reading proteins and the precise Histone Codes were quantitatively characterized. This revealed unique variations in PTM patterns between Brd and control pulldowns in HEK cells.

Figure 7:
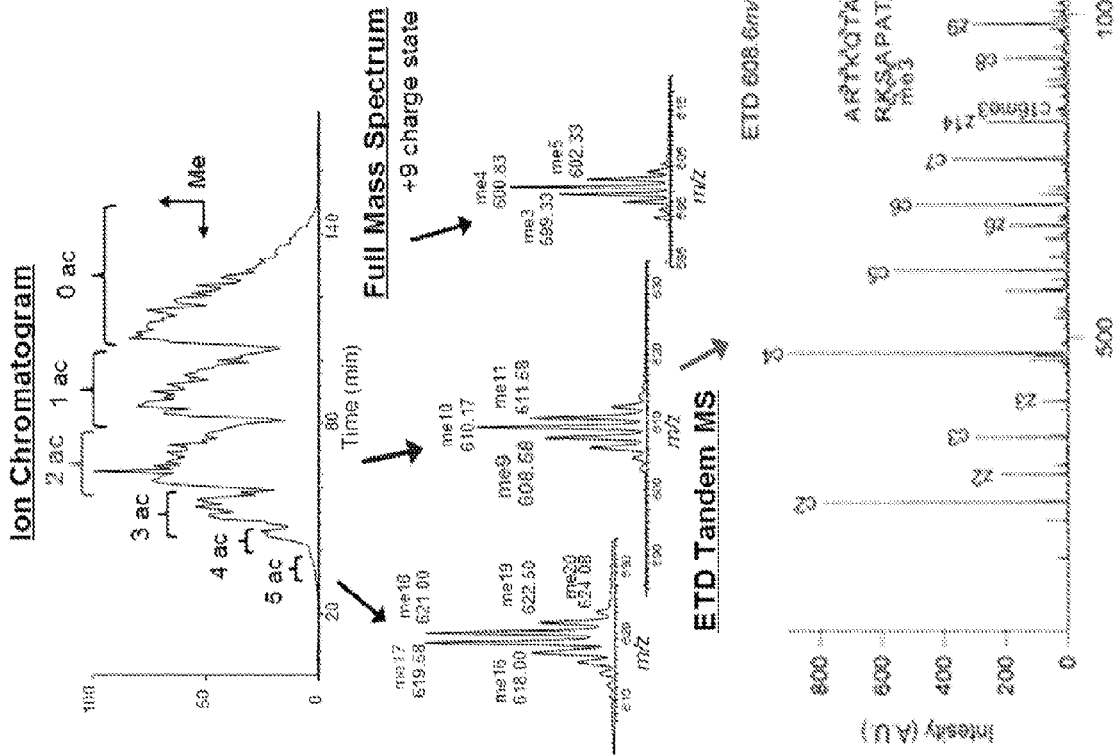
FIG. 7 illustrates highthroughput separation and MS characterization of modified combinatorial histone H3 forms.

All major combinatorial Histone Codes present in a sample can be identified and quantified in a single MS experiment with minimal sample preparation, unprecedented speed, accuracy and sensitivity. See, for example, Young, N. L.; DiMaggio, P. A.; Plazas-Mayorca, M. D.; Baliban, R. C.;

Floudas, C. A.; Garcia, B. A., High throughput characterization of combinatorial histone codes. Mol Cell Proteomics 2009, 8, (10), 2266-84, which is incorporated herein by reference as if fully set forth. This enables an on-line liquid chromatography MS method for the high-throughput characterization of the histone amino terminal tail. Referring to FIG. 7, a pH gradient driven on-line hydrophilic interaction chromatography method may be utilized coupled to electron transfer dissociation (ETD) to sequence the polypeptides and identify sites of modification. Through this method over 1000 distinctly Histone Codes on histone H3 alone (across 3 variants) on HeLa cells were discovered, a 5-fold increase in previously identified histone H3 modified forms. The method used only a single 3-4 hour mass spectrometry analysis compared to using over 100 hours of MS data acquisition time as was needed with the previous method. This raw data can be converted to a heat map image to visualize the modified forms and determine which Codes are dynamically altered from sample to sample. Additionally, as this separation has been pushed from the offline analytical scale to the on-line capillary nanoflow level, the sample requirement was decreased from 150 µg to less than 0.5 µg. The technology herein will allow for the first time to identify the entire spectrum of post-translational modifications that occur on the histones associated a particular locus. It also allows the identification of potentially new, non-histone proteins that are associated with such chromatin.

Example 8

Reverse ChIP

Sequence-specific extraction of DNA-bound histones. The sequence-specific isolation and analysis of post translational histone modifications has been achieved. In short, chromatin was prepared from cells containing the model system in the transgene 'off' state as described in FIG. 1a and Janicki S M, Tsukamoto T, Salghetti S E, Tansey W P, Sachidanandam R, Prasanth K V, Ried T, Shav-Tal Y, Bertrand E, Singer R H, Spector D L. From silencing to gene expression: real-time analysis in single cells. Cell. 2004 Mar. 5; 116(5):683-98, which is incorporated herein by reference as if fully set forth. The 256 copies of the of the lac operator sequence were then targeted at the 5' end of the construct with a single, complementary primer of the sequence 5'-AAT TGT TAT CCG CTC ACA ATT CC-3' (SEQ ID NO: 1).

In a modified protocol carried out manually, the isolation of the transgene chromatin was then achieved by combining about 5 µg total DNA with reaction buffer and the capture primer, denaturing for 2 min. at 92° C., followed by a 5 min. enzymatic extension at 64° C. with biotinylated nucleotides. The reaction mixture was then carefully incubated for 4 min. with 120 µl of our streptavidin beads for region-specific extraction. During this process, relative magnetic motion of the beads through solution ensures that even large chromosomal segments are captured with high efficiency. The chromatin was released from the beads through incubation at 80° C. for 10 min. and magnetic removal of the beads.

Figure 8:
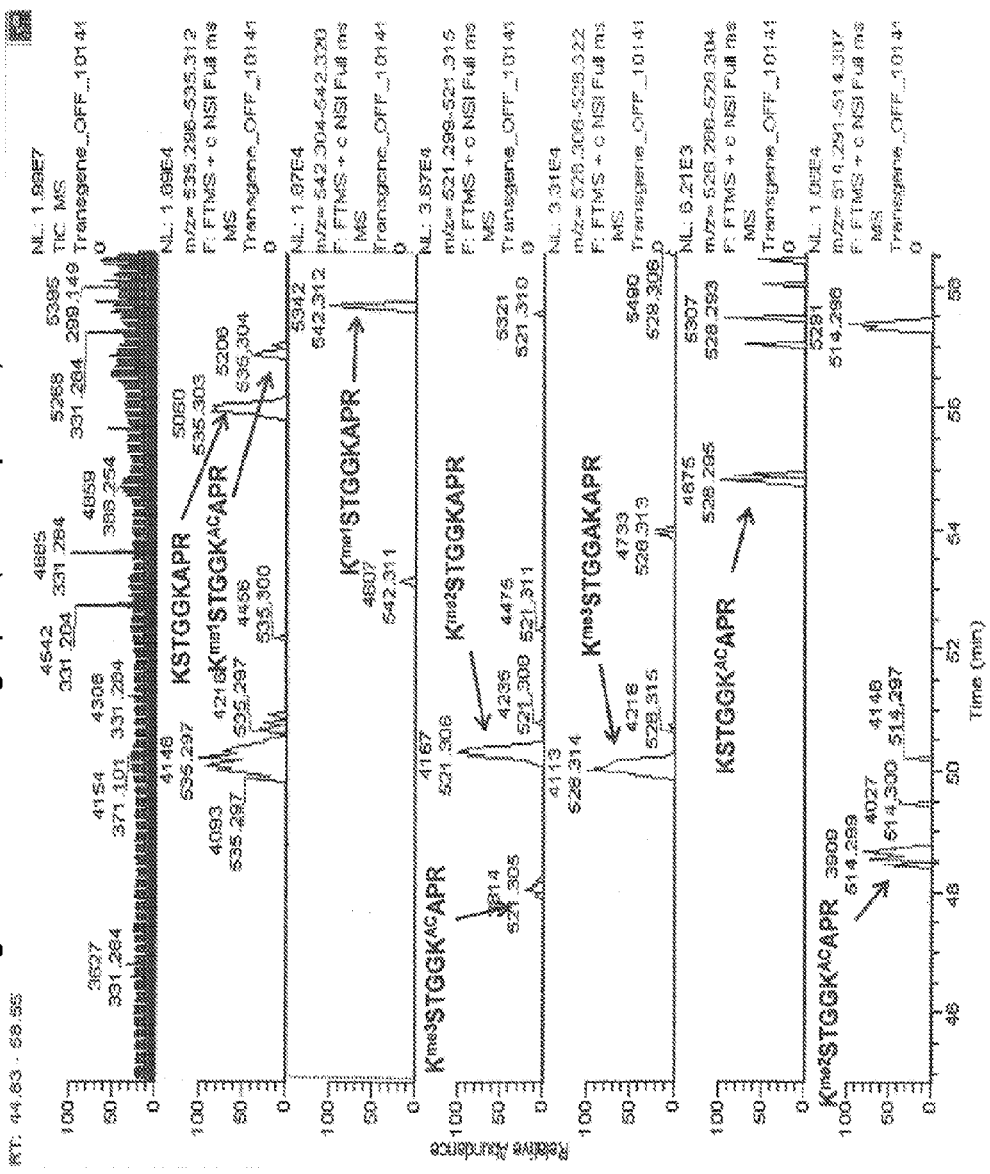
FIG. 8 illustrates analysis of Histone H3 residues 9-17.

Referring to FIG. 8, the resulting proteins present in this sample were propionylated at the unmodified lysine residues ("K"), trypsinized, C18 stage tip purified and analyzed by mass spectrometry (MS). This process selectively cuts peptides at arginine residues ("R") to a length that makes them easily detectable in a 'bottom-up' MS experiment while allowing for the combinatorial analysis of at least a few connected post-translational modifications (PTMs) that are present on the same histone molecule. The sample was then directly run on a reverse phase (C18) nanoflow HPLC and peptides were detected by electrospray-MS on a Fourier Transform Mass Spectrometry (FTMS) instrument at Princeton University. As shown in the mass chromatograms in FIG. 8, various modified forms of the peptide residues 9-17, KSTGGKAPR (SEQ ID NO: 2), from histone H3 were detected. Multiple forms of lysine methylation and acetylation on this peptide were identified and quantified. For instance, as labeled in panel 2 of FIG. 8 (red, second from the top), the peaks corresponding to the peptide containing the unmodified residues 9-17, "KSTGGKAPR" (SEQ ID NO: 2), as well as the modified form "Kme1STGGKACAPR" (SEQ ID NO: 3), where lysine residue 9 is monomethylated ("Kme1") and residue 14 is acetylated ("KAC"), were detected. In the third panel (green, third from the top), residue 9 is monomethylated, while residue 14 remains unmodified ("Kme1STGGKAPR" (SEQ ID NO: 4)). In panel 4 (dark blue, fourth from the top), the first labeled peak corresponds to a peptide where residue 9 is trimethylated and residue 14 is acetylated ("Kme3" & "KAC" in "Kme3STGGKACAPR" (SEQ ID NO: 5)), while the second labeled peak corresponds to same peptide where K9 is di-methylated and K14 is unacetylated ("Kme2STGGKAPR" (SEQ ID NO: 6)),etc. Equivalent data was obtained when analyzing residues 18-26, indicating that the approach works reproducibly for different peptides (data not shown). The fact that a specific promoter region was successfully targeted and thereby enabling isolation of downstream genes along with their attached histones demonstrates being able to target chromatin related to any gene of interest this way.

Example 9

Targeted Isolation of Disease-Associated Genomic Regions and Chromatin. Region-specific extraction (RSE) is an automated magnetic enrichment technology that selectively isolates large segments of native genomic DNA with high efficiency from specific regions of interest. Depending on the application and downstream platform that is used, DNA sequences as well as proteins that are physically linked to the targeted locus are detected. Sample analysis can be performed by Next-Generation Sequencing (NGS), conventional sequencing or genotyping, DNA microarrays, or mass spectrometry (MS). The reduction in complexity achieved by selective capture 1) Simplifies sequence assembly, 2) Reduces cost per run by increasing the number of different samples that can be run in parallel through indexing ("barcoding"), and 3) Allows epigenetic analysis by NGS and the determination of post-translational modifications (PTMs) in a gene-specific way via MS.

Figure 9:
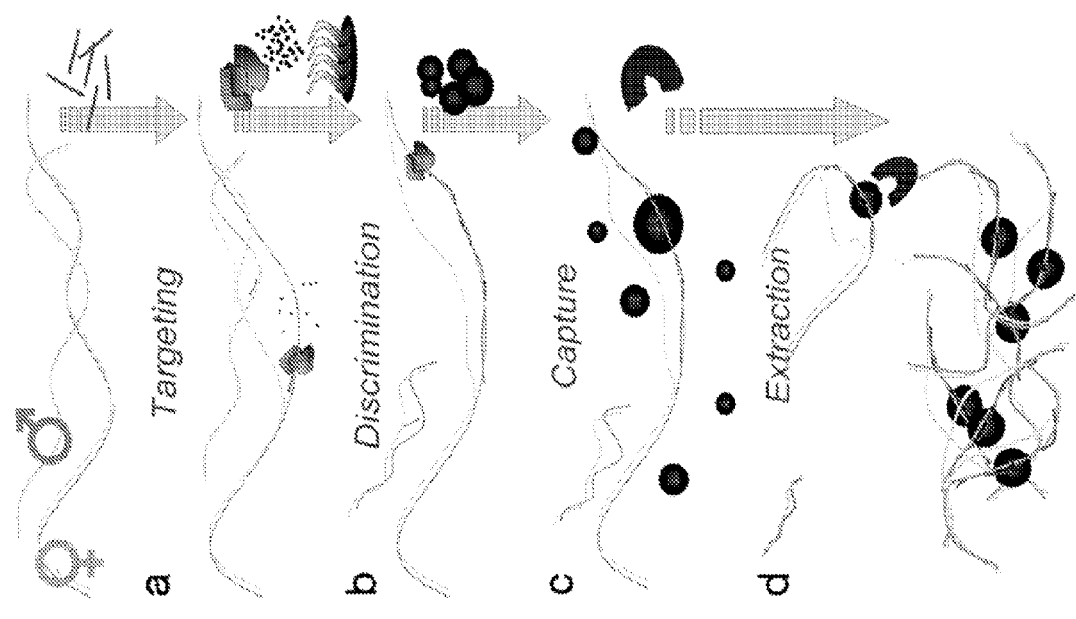
FIG. 9a illustrates capture of target sequences.
FIG. 9b illustrates an enzymatic step incorporating labels; e.g., biotin labels, only to chromosomal fragments that contain a targeted sequence or polymorphism.
FIG. 9c illustrates that capturable beads; e.g., streptavidin coated magnetic beads, isolate targeted DNA along with flanking regions by association with a label.
FIG. 9d illustrates washing other fragments away.

How HSE/RSE works. Referring to FIG. 9a, target sequences are captured by probes that hybridize to specific genomic regions or unique sequence elements such as SNPs. Referring to FIG. 9b, an enzymatic step incorporates labels; e.g., biotin labels, only to chromosomal fragments that contain the targeted sequence or polymorphism. Referring to FIG. 9c, capturable beads; e.g., streptavidin-coated magnetic beads, isolate the targeted DNA along with flanking regions by association with the label, and other fragments are washed away (FIG. 9d).

Figure 10:
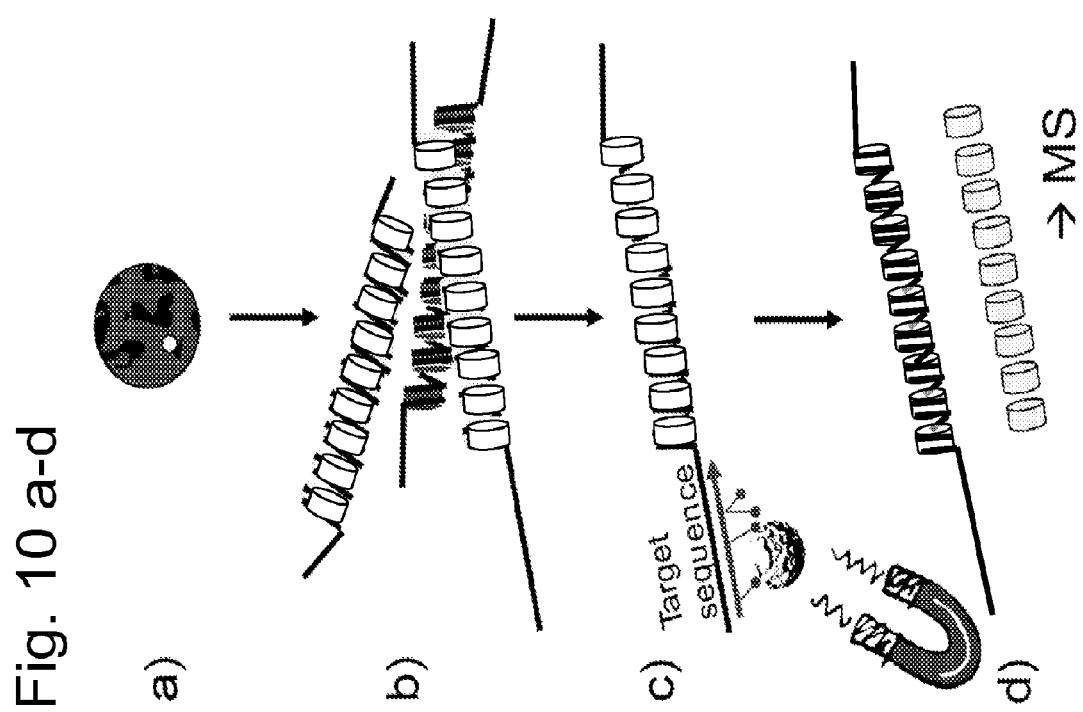
FIG. 10a illustrates cell lysis.
FIG. 10b illustrates restriction digestion.
FIG. 10c illustrates that the targeted loci may be extracted from the mixture with magnetic microparticles.
FIG. 10d illustrates proteins associated with the isolated regions that may be released and analyzed by high-end mass spectrometry.

Referring to FIGS. 10a-d, the procedure may be modified for the gene-specific isolation of chromatin. After cell lysis (FIG. 10a) and restriction digest (FIG. 10b), the targeted loci may be extracted from the mixture with magnetic microparticles (FIG. 10c). Proteins associated with the isolated regions may be released and analyzed by high-end mass spectrometry (FIG. 10d).

Post-translational modifications (PTMs) are intensely investigated because they can be causative factors for various human diseases such as cancer and neurological disorders, and the identification of their state can provide valuable data during candidate drug screening of potential histone deacetylase (HDAC) inhibitors. Currently no ability exists to conduct this in a sequence-specific, automated and potentially high-throughput manner.

Figure 11:
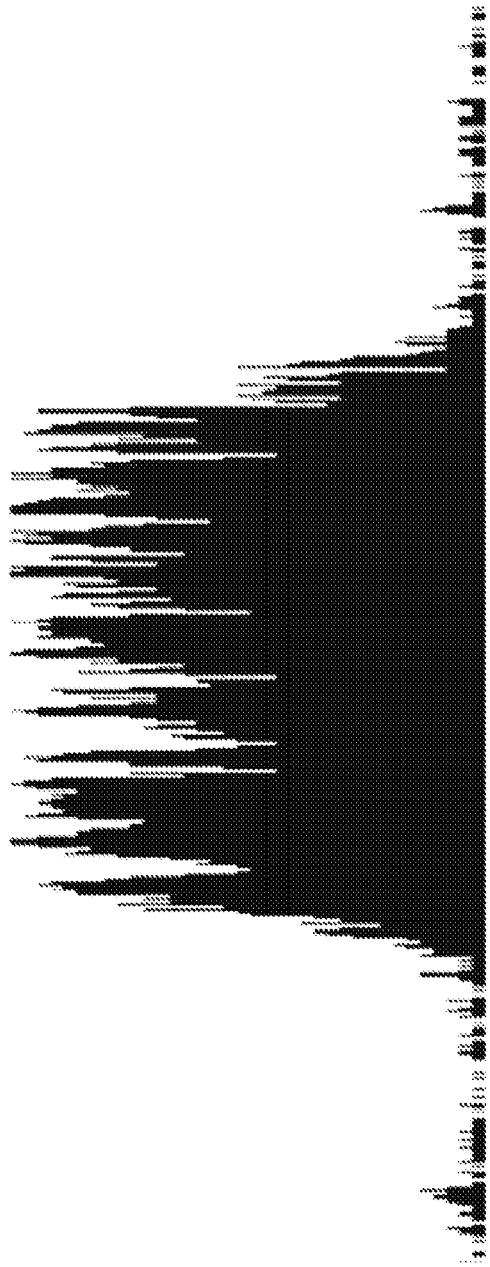
FIG. 11 illustrates data from a study where RSE followed by NGS was used to successfully detect a 31 base pair microdeletion that causes a developmental defect.
Figure 12:
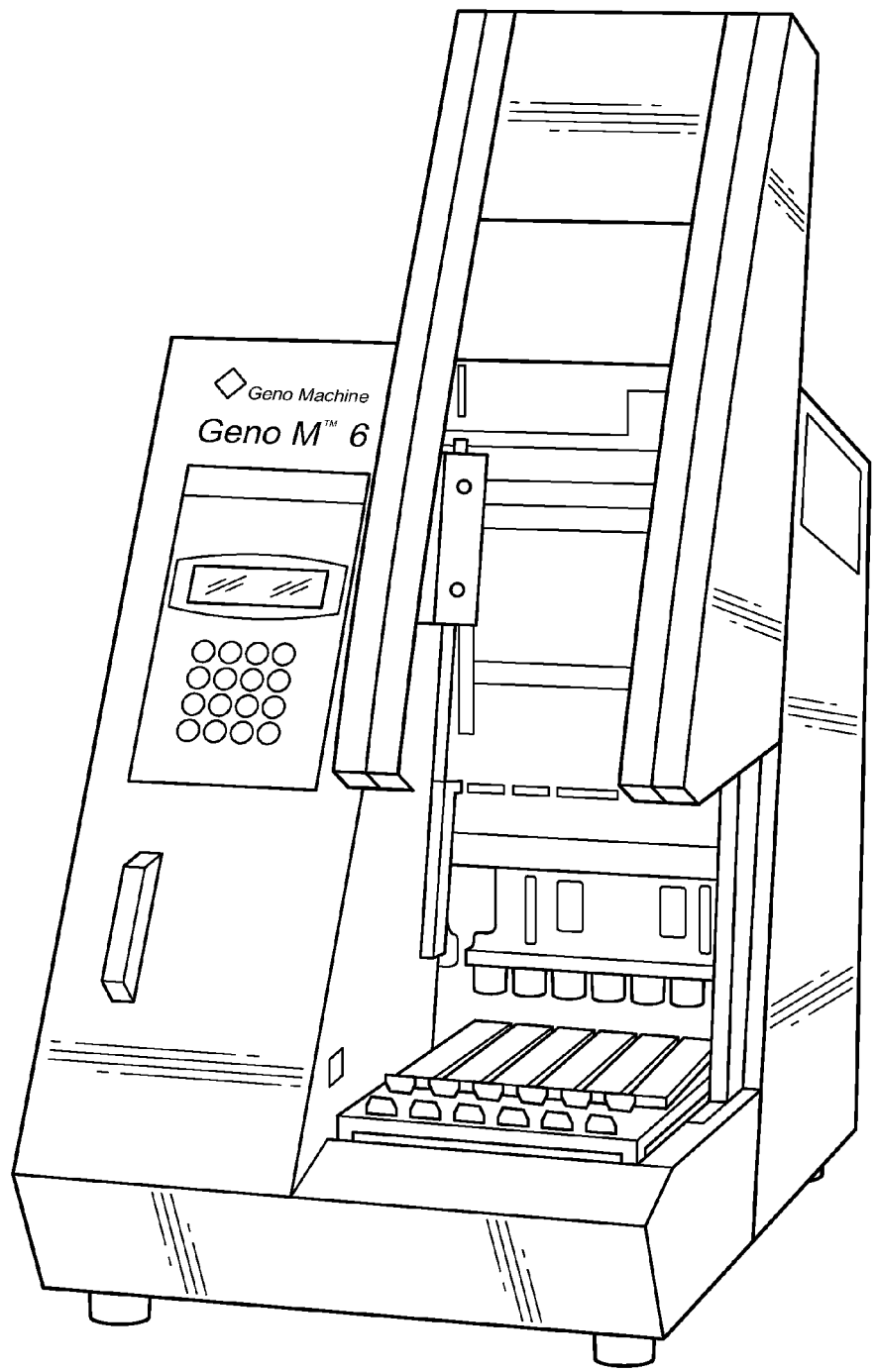
FIG. 12 illustrates automated DNA manipulation.

FIG. 11 shows data from a study where RSE followed by NGS was used to successfully detect a 31 base pair microdeletion that causes a developmental defect and had not been discovered by other means. The ability to isolate large DNA fragments in an automated way (e.g., FIG. 12) is also valuable for the use in targeted NGS paired-end read strategies, potentially involving insert sizes of 500-10,000 bases.

One advantage of RSE over other enrichment technologies is that it reliably captures large (e.g., >20 kb) chromosomal segments with a small number of probes. Other enrichment methods typically require fragmentation of the target DNA down to 100s of bases in length. The ability of RSE to directly pull down large, native genomic DNA is useful to determine linkage over large distances and accurately resolve structural variation.

RSE is used for translocation breakpoint analysis with the perspective of becoming a tool for patient stratification and reduction of adverse events for increased drug safety profiles. Haplotype-specific extraction (HSE) is used for transplantation tissue typing, forensics, mapping.

Figure 13:
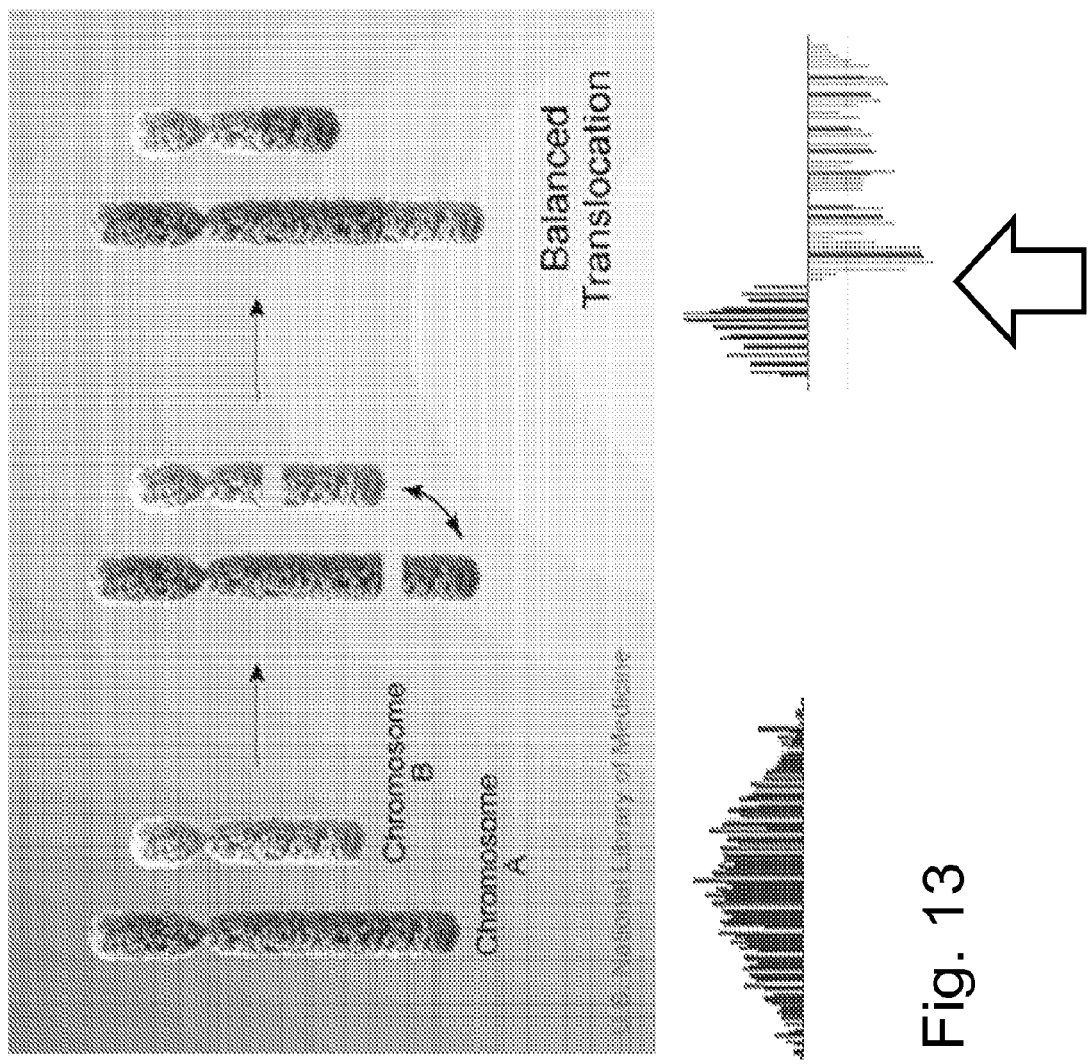
FIG. 13 illustrates how reciprocal translocation breakpoints or unknown sequence surrounding a specific target point can be detected by RSE in combination with conventional DNA typing assays or NGS.

FIG. 13 shows how reciprocal translocation breakpoints or unknown sequence surrounding a specific target point (indicated by an orange, large arrow) can be detected by RSE in combination with conventional DNA typing assays or NGS. The presence of genetic material across the breakpoint is determined from the material that is captured via the targeted insertion point or chromosomal translocation partner.

This ability is valuable for the mapping of retroviral and transposon insertions, such as for T-DNA (transfer DNA)-based cloning and border rescue. The T-DNA method is used widely to study gene function in plants, and has important uses in agricultural genetics. The inserted T-DNA sequence effectively 'tags' the inserted gene, thus allowing for its isolation along with any surrounding loci.

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of isolating a nucleic acid binding protein comprising:
   providing a sample that may contain a first nucleic acid having a nucleic acid binding protein bound thereon;
   providing a second nucleic acid that has an affinity label and is capable of binding to the first nucleic acid to form a complex;
   isolating the complex through binding of the affinity label to a moiety capable of binding the affinity label; and
   obtaining the nucleic acid binding protein from the isolated complex.

2. The method of claim 1, wherein the first nucleic acid is a deoxyribonucleic acid.

3. The method of claim 1, wherein the nucleic acid binding protein is a histone.

4. The method of claim 1, wherein the nucleic acid binding protein is a post-translationally modified histone.

5. The method of claim 1, wherein the nucleic acid binding protein is a post-translationally modified histone and the post-translational modification is acetylation.

6. The method of claim 1, wherein the affinity label is biotin.

7. The method of claim 1, wherein the moiety capable of binding the affinity label includes streptavidin.

8. The method of claim 1, wherein the moiety capable of binding the affinity label includes streptavidin-coated magnetic microparticles.

9. The method of claim 1, further comprising providing conditions for hybridization of the first nucleic acid to the second nucleic acid.

10. The method of claim 1, wherein the step of isolating the complex through binding of the affinity label to a moiety capable of binding the affinity label further includes providing a magnet.

11. The method of claim 1, wherein the step of obtaining the nucleic acid binding protein from the isolated complex includes dissociating the nucleic acid binding protein from the first nucleic acid.

12. A method of analyzing nucleic acid binding protein post-translational modification comprising:
    providing a sample that may contain a first nucleic acid having a nucleic acid binding protein bound thereon;
    providing a second nucleic acid that has an affinity label and is capable of binding to the first nucleic acid to form a complex;
    isolating the complex through binding of the affinity label to a moiety capable of binding the affinity label;
    obtaining the nucleic acid binding protein from the isolated complex; and
    analyzing the nucleic acid binding protein.

13. The method of claim 12, wherein the first nucleic acid is a deoxyribonucleic acid.

14. The method of claim 12, wherein the nucleic acid binding protein is a histone.

15. The method of claim 12, wherein the nucleic acid binding protein is a post-translationally modified histone.

16. The method of claim 12, wherein the nucleic acid binding protein is a post-translationally modified histone and the post-translational modification is acetylation.

17. The method of claim 12, wherein the affinity label is biotin.

18. The method of claim 12, wherein the moiety capable of binding the affinity label includes streptavidin.

19. The method of claim 12, wherein the moiety capable of binding the affinity label includes streptavidin-coated magnetic microparticles.

20. The method of claim 12, further comprising providing conditions for hybridization of the first nucleic acid to the second nucleic acid.

21. The method of claim 12, wherein the step of isolating the complex through binding of the affinity label to a moiety capable of binding the affinity label further includes providing a magnet.

22. The method of claim 12, wherein the step of obtaining the nucleic acid binding protein from the isolated complex includes dissociating the nucleic acid binding protein from the first nucleic acid.

23. The method of claim 12, wherein the step of analyzing the nucleic acid binding protein includes high-end combinatorial mass spectrometry.

24. A method of screening drug candidates comprising:
providing a sample including a drug candidate;
providing a second nucleic acid that has an affinity label and is capable of binding to the sample to form a complex;
isolating the complex through binding of the affinity label to a moiety capable of binding the affinity label; and
obtaining a first nucleic acid binding protein from the isolated complex;
providing a control sample including a control substance;
providing a third nucleic acid that has an affinity label and is capable of binding to the control sample to form a second complex;
isolating the second complex through binding of the affinity label to a moiety capable of binding the affinity label;
obtaining a second nucleic acid binding protein from the isolated second complex; and
comparing a first nucleic acid binding protein post-translational modification profile from the sample to a second nucleic acid binding protein post-translational modification profile from the control sample.

25. The method of claim 24, wherein the drug candidate is a compound that alters the activity of histone acetyltransferase.

26. The method of claim 25, wherein the compound that alters the activity of histone acetyltransferase is an inhibitor of histone acetyltransferase.

27. The method of claim 25, wherein the compound that alters the activity of histone acetyltransferase is an allosteric affector of histone acetyltransferase.

28. The method of claim 24, wherein the drug candidate is a compound that alters the activity of histone deacetylase.

29. The method of claim 28, wherein the compound that alters the activity of histone deacetylase is an inhibitor of histone deacetylase.

30. The method of claim 28, wherein the compound that alters the activity of histone deacetylase is an allosteric affector of histone deacetylase.

* * * * *

SEQUENCE LISTING

```
<160> NUMBER OF SEQ ID NOS: 17

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aattgttatc cgctcacaat tcc                                              23

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ser Thr Gly Gly Lys Ala Pro Arg
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Monomethylated-Lys
<220> FEATURE:
```

```
<221> NAME/KEY: MOD_RES
<222> LOCATION: (6)..(6)
<223> OTHER INFORMATION: Acetylated-Lys

<400> SEQUENCE: 3

Lys Ser Thr Gly Gly Lys Ala Pro Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Monomethylated-Lys

<400> SEQUENCE: 4

Lys Ser Thr Gly Gly Lys Ala Pro Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trimethylated-Lys
<220> FEATURE:
<221> NAME/KEY: MOD_RES
<222> LOCATION: (6)..(6)
<223> OTHER INFORMATION: Acetylated-Lys

<400> SEQUENCE: 5

Lys Ser Thr Gly Gly Lys Ala Pro Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dimethylated-Lys

<400> SEQUENCE: 6

Lys Ser Thr Gly Gly Lys Ala Pro Arg
1               5

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattgttatc cgctcac                                                  17
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aattccacat gtggccaca                                                    19

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aattccacat gtggaattcc aca                                               23

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgagtttac cactccctat cagtgataga gaaaagtgaa ag                          42

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcgtcgaccg ggtcgaggta g                                                 21

<210> SEQ ID NO 12
<211> LENGTH: 14996
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ctcgagggat cgacctcgga ctctagaggc gccgaattcc acaaattgtt atccgctcac        60
aattccacat gtggccacaa attgttatcc gctcacaatt ccacatgtgg ccacaaattg       120
ttatccgctc acaattccac atgtggccac aaattgttat ccgctcacaa ttccacatgt       180
ggccacaaat tgttatccgc tcacaattcc acatgtggcc acaaattgtt atccgctcac       240
aattccacat gtggccacaa attgttatcc gctcacaatt ccacatgtgg ccacaaattg       300
ttatccgctc acaattccac atgtggaatt ccacaaattg ttatccgctc acaattccac       360
atgtggccac aaattgttat ccgctcacaa ttccacatgt ggccacaaat tgttatccgc       420
tcacaattcc acatgtggcc acaaattgtt atccgctcac aattccacat gtggccacaa       480

```
attgttatcc gctcacaatt ccacatgtgg ccacaaattg ttatccgctc acaattccac    540
atgtggccac atcgtcgacc gggtcgaggt agaattccac atgtggaatt ccacaaattc    600
cacatgtgga attccacaaa ttccacatgt ggaattccac aaattccaca tgtggaattc    660
cacaaattcc acatgtggaa ttccacaaat tccacatgtg gaattccaca aattccacat    720
gtggaattcc acaaattcca catgtggaat tccacaaatt ccacatgtgg aattccacaa    780
attccacatg tggaattcca caaattccac atgtggaatt ccacaaattc cacatgtgga    840
attccacaaa ttccacatgt ggaattccac aaattccaca tgtggaattc cacaaattcc    900
acatgtggaa ttccacaaat tccacatgtg gaattccaca aattccacat gtggaattcc    960
acaaattcca catgtggaat tccacaaatt ccacatgtgg aattccacaa attccacatg   1020
tggaattcca caaattccac atgtggaatt ccacaaattc cacatgtgga attccacaaa   1080
ttccacatgt ggaattccac aaattccaca tgtggaattc cacaaattcc acatgtggaa   1140
ttccacaaat tccacatgtg gaattccaca aattccacat gtggaattcc acaaattcca   1200
catgtggaat tccacaaatt ccacatgtgg aattccacaa attccacatg tggaattcca   1260
caaattccac atgtggaatt ccacaaattc cacatgtggc cacaaattcc acatgtggcc   1320
acaaattcca catgtggcca caaattccac atgtggccac aaattccaca tgtggccaca   1380
aattccacat gtggccacaa attccacatg tggccacaaa ttccacatgt ggccacaaat   1440
tccacatgtg gccacaaatt ccacatgtgg ccacaaattc cacatgtggc cacaaattcc   1500
acatgtggcc acaaattcca catgtggcca caaattccac atgtggccac aaattccaca   1560
tgtggccaca aattccacat gtggccacaa attccacatg tggccacaaa ttccacatgt   1620
ggccacaaat tccacatgtg gccacaaatt ccacatgtgg ccacaaattc cacatgtggc   1680
cacaaattcc acatgtggcc acaaattcca catgtggcca caaattccac atgtggccac   1740
aaattccaca tgtggccaca aattccacat gtggccacaa attccacatg tggccacaaa   1800
ttccacatgt ggccacaaat tccacatgtg gccacaaatt ccacatgtgg ccacaaattc   1860
cacatgtggc cacaaattcc acatgtggcc acaaattcca catgtggcca caaattccac   1920
atgtggccac aaattccaca tgtggccaca aattccacat gtggccacaa attccacatg   1980
tggccacaaa ttccacatgt ggccacaaat tccacatgtg gccacaaatt ccacatgtgg   2040
ccacaaattc cacatgtggc cacaaattcc acatgtggcc acaaattcca catgtggcca   2100
caaattccac atgtggccac aaattccaca tgtggccaca aattccacat gtggccacaa   2160
attccacatg tggccacaaa ttccacatgt ggccacaaat tccacatgtg gccacaaatt   2220
ccacatgtgg ccacaaattc cacatgtggc cacaaattcc acatgtggcc acaaattcca   2280
catgtggcca caaattccac atgtggccac aaattccaca tgtggccaca aattccacat   2340
gtggccacaa attccacatg tggccacaaa ttccacatgt ggccacaaat tccacatgtg   2400
gccacaaatt ccacatgtgg ccacaaattc cacatgtggc cacaaattcc acatgtggcc   2460
acaaattcca catgtggcca caaattccac atgtggccac aaattccaca tgtggccaca   2520
aattccacat gtggccacaa attccacatg tggccacaaa ttccacatgt ggccacaaat   2580
tccacatgtg gccacaaatt ccacatgtgg ccacaaattc cacatgtggc cacaaattcc   2640
acatgtggcc acaaattcca catgtggcca caaattccac atgtggccac aaattccaca   2700
tgtggccaca aattccacat gtggccacaa attccacatg tggccacaaa ttccacatgt   2760
ggccacaaat tccacatgtg gccacaaatt ccacatgtgg ccacaaattc cacatgtggc   2820
```

```
cacaaattcc acatgtggcc acaaattcca catgtggcca caaattccac atgtggccac    2880
aaattccaca tgtggccaca aattccacat gtggccacaa attccacatg tggccacaaa    2940
ttccacatgt ggccacaaat tccacatgtg gccacaaatt ccacatgtgg ccacaaattc    3000
cacatgtggc cacaaattcc acatgtggcc acaaattcca catgtggcca caaattccac    3060
atgtggccac aaattccaca tgtggccaca aattccacat gtggccacaa attccacatg    3120
tggccacaaa ttccacatgt ggccacaaat tccacatgtg gccacaaatt ccacatgtgg    3180
ccacaaattc cacatgtggc cacaaattcc acatgtggcc acaaattcca catgtggcca    3240
caaattccac atgtggccac aaattccaca tgtggccaca aattccacat gtggccacaa    3300
attccacatg tggccacaaa ttccacatgt ggccacaaat tccacatgtg gccacaaatt    3360
ccacatgtgg ccacaaattc cacatgtggc cacaaattcc acatgtggcc acaaattcca    3420
catgtggcca caaattccac atgtggccac aaattccaca tgtggccaca aattccacat    3480
gtggccacaa attccacatg tggccacaaa ttccacatgt ggccacaaat tccacatgtg    3540
gccacaaatt ccacatgtgg ccacaaattc cacatgtggc cacaaattcc acatgtggcc    3600
acaaattcca catgtggcca caaattccac atgtggccac aaattccaca tgtggccaca    3660
aattccacat gtggccacaa attccacatg tggccacaaa ttccacatgt ggccacaaat    3720
tccacatgtg gccacaaatt ccacatgtgg ccacaaattc cacatgtggc cacaaattcc    3780
acatgtggcc acaaattcca catgtggcca caaattccac atgtggccac aaattccaca    3840
tgtggccaca aattccacat gtggccacaa attccacatg tggccacaaa ttccacatgt    3900
ggccacaaat tccacatgtg gccacaaatt ccacatgtgg ccacaaattc cacatgtggc    3960
cacaaattcc acatgtggcc acaaattcca catgtggcca caaattccac atgtggccac    4020
aaattccaca tgtggccaca aattccacat gtggccacaa attccacatg tggccacaaa    4080
ttccacatgt ggccacaaat tccacatgtg gccacaaatt ccacatgtgg ccacaaattc    4140
cacatgtggc cacaaattcc acatgtggcc acaaattcca catgtggcca caaattccac    4200
atgtggccac aaattccaca tgtggccaca aattccacat gtggccacaa attccacatg    4260
tggccacaaa ttccacatgt ggccacaaat tccacatgtg gccacaaatt ccacatgtgg    4320
ccacaaattc cacatgtggc cacaaattcc acatgtggcc acaaattcca catgtggcca    4380
caaattccac atgtggccac aaattccaca tgtggccaca aattccacat gtggccacaa    4440
attccacatg tggccacaaa ttccacatgt ggccacaaat tccacatgtg gccacaaatt    4500
ccacatgtgg ccacaaattc cacatgtggc cacaaattcc acatgtggcc acaaattcca    4560
catgtggcca caaattccac atgtggccac aaattccaca tgtggccaca aattccacat    4620
gtggccacaa attccacatg tggccacaaa ttccacatgt ggccacaaat tccacatgtg    4680
gccacaaatt ccacatgtgg ccacaaattc cacatgtggc cacaaattcc acatgtggcc    4740
acaaattcca catgtggcca caaattccac atgtggccac aaattccaca tgtggccaca    4800
aattccacat gtggccacaa attccacatg tggccacaaa ttccacatgt ggccacaaat    4860
tccacatgtg gccacaaatt ccacatgtgg ccacaaattc cacatgtggc cacaaattcc    4920
acatgtggcc acaaattcca catgtggcca caaattccac atgtggccac aaattccaca    4980
tgtggccaca aattccacat gtggccacaa attccacatg tggccacaaa ttccacatgt    5040
ggccacaaat tccacatgtg gccacaaatt ccacatgtgg ccacaaattc cacatgtggc    5100
cacaaattcc acatgtggcc acaaattcca catgtggcca caaattccac atgtggccac    5160
aaattccaca tgtggccaca aattccacat gtggccacaa attccacatg tggccacaaa    5220
```

```
ttccacatgt ggccacaaat tccacatgtg gccacaaatt ccacatgtgg ccacaaattc    5280
cacatgtggc cacaaattcc acatgtggcc acaaattcca catgtggcca caaattccac    5340
atgtggccac aaattccaca tgtggccaca attccacatg tggccacaa attccacatg     5400 tggccacaaa ttccacatgt ggccacaaat tccacatgtg gccacaaatt ccacatgtgg    5460
ccacaaattc cacatgtggc cacaaattcc acatgtggcc acaaattcca catgtggca    5520 caaattccac atgtggccac aaattgttat ccgctcacaa ttgttatccg ctcacaattg    5580
ttatccgctc acaattgtta tccgctcaca attgttatcc gctcacaatt gttatccgct    5640
cacaattgtt atccgctcac aattgttatc cgctcacaat tgttatccgc tcacaattgt    5700
tatccgctca caattgttat ccgctcacaa ttgttatccg ctcacaattg ttatccgctc    5760
acaattgtta tccgctcaca attgttatcc gctcacaatt gttatccgct cacaattgtt    5820
atccgctcac aattgttatc cgctcacaat tgttatccgc tcacaattgt tatccgctca    5880
caattgttat ccgctcacaa ttgttatccg ctcacaattg ttatccgctc acaattgtta    5940
tccgctcaca attgttatcc gctcacaatt gttatccgct cacaattgtt atccgctcac    6000
aattgttatc cgctcacaat tgttatccgc tcacaattgt tatccgctca caattgttat    6060
ccgctcacaa ttgttatccg ctcacaattg ttatccgctc acaattgtta tccgctcaca    6120
attgttatcc gctcacaatt gttatccgct cacaattgtt atccgctcac aattgttatc    6180
cgctcacaat tgttatccgc tcacaattgt tatccgctca caattgttat ccgctcacaa    6240
ttgttatccg ctcacaattg ttatccgctc acaattgtta tccgctcaca attgttatcc    6300
gctcacaatt gttatccgct cacaattgtt atccgctcac aattgttatc cgctcacaat    6360
tgttatccgc tcacaattgt tatccgctca caattgttat ccgctcacaa ttgttatccg    6420
ctcacaattg ttatccgctc acaattgtta tccgctcaca attgttatcc gctcacaatt    6480
gttatccgct cacaattgtt atccgctcac aattgttatc cgctcacaat tgttatccgc    6540
tcacaattgt tatccgctca caattgttat ccgctcacaa ttgttatccg ctcacaattg    6600
ttatccgctc acaattgtta tccgctcaca attgttatcc gctcacaatt gttatccgct    6660
cacaattgtt atccgctcac aattgttatc cgctcacaat tgttatccgc tcacaattgt    6720
tatccgctca caattgttat ccgctcacaa ttgttatccg ctcacaattg ttatccgctc    6780
acaattgtta tccgctcaca attgttatcc gctcacaatt gttatccgct cacaattgtt    6840
atccgctcac aattgttatc cgctcacaat tgttatccgc tcacaattgt tatccgctca    6900
caattgttat ccgctcacaa ttgttatccg ctcacaattg ttatccgctc acaattgtta    6960
tccgctcaca attgttatcc gctcacaatt gttatccgct cacaattgtt atccgctcac    7020
aattgttatc cgctcacaat tgttatccgc tcacaattgt tatccgctca caattgttat    7080
ccgctcacaa ttgttatccg ctcacaattg ttatccgctc acaattgtta tccgctcaca    7140
attgttatcc gctcacaatt gttatccgct cacaattgtt atccgctcac aattgttatc    7200
cgctcacaat tgttatccgc tcacaattgt tatccgctca caattgttat ccgctcacaa    7260
ttgttatccg ctcacaattg ttatccgctc acaattgtta tccgctcaca attgttatcc    7320
gctcacaatt gttatccgct cacaattgtt atccgctcac aattgttatc cgctcacaat    7380
tgttatccgc tcacaattgt tatccgctca caattgttat ccgctcacaa ttgttatccg    7440
ctcacaattg ttatccgctc acaattgtta tccgctcaca attgttatcc gctcacaatt    7500
gttatccgct cacaattgtt atccgctcac aattgttatc cgctcacaat tgttatccgc    7560
```

```
tcacaattgt tatccgctca caattgttat ccgctcacaa ttgttatccg ctcacaattg   7620
ttatccgctc acaattgtta tccgctcaca attgttatcc gctcacaatt gttatccgct   7680
cacaattgtt atccgctcac aattgttatc cgctcacaat tgttatccgc tcacaattgt   7740
tatccgctca caattgttat ccgctcacaa ttgttatccg ctcacaattg ttatccgctc   7800
acaattgtta tccgctcaca attgttatcc gctcacaatt gttatccgct cacaattgtt   7860
atccgctcac aattgttatc cgctcacaat tgttatccgc tcacaattgt tatccgctca   7920
caattgttat ccgctcacaa ttgttatccg ctcacaattg ttatccgctc acaattgtta   7980
tccgctcaca attgttatcc gctcacaatt gttatccgct cacaattgtt atccgctcac   8040
aattgttatc cgctcacaat tgttatccgc tcacaattgt tatccgctca caattgttat   8100
ccgctcacaa ttgttatccg ctcacaattg ttatccgctc acaattgtta tccgctcaca   8160
attgttatcc gctcacaatt gttatccgct cacaattgtt atccgctcac aattgttatc   8220
cgctcacaat tgttatccgc tcacaattgt tatccgctca caattgttat ccgctcacaa   8280
ttgttatccg ctcacaattg ttatccgctc acaattgtta tccgctcaca attgttatcc   8340
gctcacaatt gttatccgct cacaattgtt atccgctcac aattgttatc cgctcacaat   8400
tgttatccgc tcacaattgt tatccgctca caattgttat ccgctcacaa ttgttatccg   8460
ctcacaattg ttatccgctc acaattgtta tccgctcaca attgttatcc gctcacaatt   8520
gttatccgct cacaattgtt atccgctcac aattgttatc cgctcacaat tgttatccgc   8580
tcacaattgt tatccgctca caattgttat ccgctcacaa ttgttatccg ctcacaattg   8640
ttatccgctc acaattgtta tccgctcaca attgttatcc gctcacaatt gttatccgct   8700
cacaattgtt atccgctcac aattgttatc cgctcacaat tgttatccgc tcacaattgt   8760
tatccgctca caattgttat ccgctcacaa ttgttatccg ctcacaattg ttatccgctc   8820
acaattgtta tccgctcaca attgttatcc gctcacaatt gttatccgct cacaattgtt   8880
atccgctcac aattgttatc cgctcacaat tgttatccgc tcacaattgt tatccgctca   8940
caattgttat ccgctcacaa ttgttatccg ctcacaattg ttatccgctc acaattgtta   9000
tccgctcaca attgttatcc gctcacaatt gttatccgct cacaattgtt atccgctcac   9060
aattgttatc cgctcacaat tgttatccgc tcacaattgt tatccgctca caattgttat   9120
ccgctcacaa ttgttatccg ctcacaattg ttatccgctc acaattgtta tccgctcaca   9180
attgttatcc gctcacaatt gttatccgct cacaattgtt atccgctcac aattgttatc   9240
cgctcacaat tgttatccgc tcacaattgt tatccgctca caattgttat ccgctcacaa   9300
ttgttatccg ctcacaattg ttatccgctc acaattgtta tccgctcaca attgttatcc   9360
gctcacaatt gttatccgct cacaattgtt atccgctcac aattgttatc cgctcacaat   9420
tgttatccgc tcacaattgt tatccgctca caattgttat ccgctcacaa ttgttatccg   9480
ctcacaattg ttatccgctc acaattgtta tccgctcaca attgttatcc gctcacaatt   9540
gttatccgct cacaattgtt atccgctcac aattgttatc cgctcacaat tgttatccgc   9600
tcacaattgt tatccgctca caattgttat ccgctcacaa ttgttatccg ctcacaattg   9660
ttatccgctc acaattgtta tccgctcaca attgttatcc gctcacaatt gttatccgct   9720
cacaattgtt atccgctcac aattgttatc cgctcacaat tgttatccgc tcacaattgt   9780
tatccgctca caattgttat ccgctcacaa ttgttatccg ctcacaattg ttatccgctc   9840
acaattgtta tccgctcaca attgttatcc gctcacaatt gttatccgct cacctcacaa   9900
ttccacatgt ggaattccac aaattgttat ccgctcacaa ttccacatgt ggccacaaat   9960
```

```
tgttatccgc tcacaattcc acatgtggcc acaaattgtt atccgctcac aattccacat    10020
gtggccacaa attgttatcc gctcacaatt ccacatgtgg ccacaaattg ttatccgctc    10080
acaattccac atgtggccac aaattgttat ccgctcacaa ttccacatgt ggccacaaat    10140
tgttatccgc tcacaattcc acatgtggcc acaaattgtt atccgctcac aattccacat    10200
gtggaattcc tcgatccctc gagtttacca ctccctatca gtgatagaga aaagtgaaag    10260
tcgagtttac cactccctat cagtgataga gaaaagtgaa agtcgagttt accactccct    10320
atcagtgata gagaaaagtg aaagtcgagt ttaccactcc ctatcagtga tagagtcgtc    10380
gaccgggtcg aggtagtcga gtttaccact ccctatcagt gatagagaaa agtgaaagtc    10440
gagtttacca ctccctatca gtgatagaga aaagtgaaag tcgagtttac cactccctat    10500
cagtgataga gaaaagtgaa agtcgagttt accactccct atcagtgata gagaaaagtg    10560
aaagtcgagt ttaccactcc ctatcagtga tagagaaaag tgaaagtcga gtttaccact    10620
ccctatcagt gatagagaaa agtgaaagtc gagtttacca ctccctatca gtgatagaga    10680
aaagtgaaag tcgagtttac cactccctat cagtgataga gaaaagtgaa agtcgagttt    10740
accactccct atcagtgata gagaaaagtg aaagtcgagt ttaccactcc ctatcagtga    10800
tagagaaaag tgaaagtcga gtttaccact ccctatcagt gatagagaaa agtgaaagtc    10860
gagtttacca ctccctatca gtgatagaga aaagtgaaag tcgagtttac cactccctat    10920
cagtgataga gaaaagtgaa agtcgagttt accactccct atcagtgata gagaaaagtg    10980
aaagtcgagt ttaccactcc ctatcagtga tagagaaaag tgaaagtcga gtttaccact    11040
ccctatcagt gatagagaaa agtgaaagtc gagtttacca ctccctatca gtgatagaga    11100
aaagtgaaag tcgagtttac cactccctat cagtgataga gaaaagtgaa agtcgagttt    11160
accactccct atcagtgata gagaaaagtg aaagtcgagt ttaccactcc ctatcagtga    11220
tagagaaaag tgaaagtcga gtttaccact ccctatcagt gatagagaaa agtgaaagtc    11280
gagtttacca ctccctatca gtgatagaga aaagtgaaag tcgagtttac cactccctat    11340
cagtgataga gaaaagtgaa agtcgagttt accactccct atcagtgata gagaaaagtg    11400
aaagtcgagt ttaccactcc ctatcagtga tagagaaaag tgaaagtcga gtttaccact    11460
ccctatcagt gatagagaaa agtgaaagtc gagtttacca ctccctatca gtgatagaga    11520
aaagtgaaag tcgagtttac cactccctat cagtgataga gaaaagtgaa agtcgagttt    11580
accactccct atcagtgata gagaaaagtg aaagtcgagt ttaccactcc ctatcagtga    11640
tagagaaaag tgaaagtcga gtttaccact ccctatcagt gatagagaaa agtgaaagtc    11700
gagtttacca ctccctatca gtgatagaga aaagtgaaag tcgagtttac cactccctat    11760
cagtgataga gaaaagtgaa agtcgagttt accactccct atcagtgata gagaaaagtg    11820
aaagtcgagt ttaccactcc ctatcagtga tagagaaaag tgaaagtcga gtttaccact    11880
ccctatcagt gatagagaaa agtgaaagtc gagtttacca ctccctatca gtgatagaga    11940
aaagtgaaag tcgagtttac cactccctat cagtgataga gaaaagtgaa agtcgagttt    12000
accactccct atcagtgata gagaaaagtg aaagtcgagt ttaccactcc ctatcagtga    12060
tagagaaaag tgaaagtcga gtttaccact ccctatcagt gatagagaaa agtgaaagtc    12120
gagtttacca ctccctatca gtgatagaga aaagtgaaag tcgagtttac cactccctat    12180
cagtgataga gaaaagtgaa agtcgagttt accactccct atcagtgata gagaaaagtg    12240
aaagtcgagt ttaccactcc ctatcagtga tagagaaaag tgaaagtcga gtttaccact    12300
```

-continued

```
ccctatcagt gatagagaaa agtgaaagtc gagtttacca ctccctatca gtgatagaga      12360
aaagtgaaag tcgagtttac cactccctat cagtgataga gaaaagtgaa agtcgagttt      12420
accactccct atcagtgata gagaaaagtg aaagtcgagt ttaccactcc ctatcagtga      12480
tagagaaaag tgaaagtcga gtttaccact ccctatcagt gatagagaaa agtgaaagtc      12540
gagtttacca ctccctatca gtgatagaga aaagtgaaag tcgagtttac cactccctat      12600
cagtgataga gaaaagtgaa agtcgagttt accactccct atcagtgata gagaaaagtg      12660
aaagtcgagt ttaccactcc ctatcagtga tagagaaaag tgaaagtcga gtttaccact      12720
ccctatcagt gatagagaaa agtgaaagtc gagtttacca ctccctatca gtgatagaga      12780
aaagtgaaag tcgagtttac cactccctat cagtgataga gaaaagtgaa agtcgagttt      12840
accactccct atcagtgata gagaaaagtg aaagtcgagt ttaccactcc ctatcagtga      12900
tagagaaaag tgaaagtcga gtttaccact ccctatcagt gatagagaaa agtgaaagtc      12960
gagtttacca ctccctatca gtgatagaga aaagtgaaag tcgagtttac cactccctat      13020
cagtgataga gaaaagtgaa agtcgagttt accactccct atcagtgata gagaaaagtg      13080
aaagtcgagt ttaccactcc ctatcagtga tagagaaaag tgaaagtcga gtttaccact      13140
ccctatcagt gatagagaaa agtgaaagtc gagtttacca ctccctatca gtgatagaga      13200
aaagtgaaag tcgagtttac cactccctat cagtgataga gaaaagtgaa agtcgagttt      13260
accactccct atcagtgata gagaaaagtg aaagtcgagt ttaccactcc ctatcagtga      13320
tagagaaaag tgaaagtcga gtttaccact ccctatcagt gatagagaaa agtgaaagtc      13380
gagtttacca ctccctatca gtgatagaga aaagtgaaag tcgagtttac cactccctat      13440
cagtgataga gaaaagtgaa agtcgagttt accactccct atcagtgata gagaaaagtg      13500
aaagtcgagt ttaccactcc ctatcagtga tagagaaaag tgaaagtcga gtttaccact      13560
ccctatcagt gatagagaaa agtgaaagtc gagtttacca ctccctatca gtgatagaga      13620
aaagtgaaag tcgagtttac cactccctat cagtgataga gaaaagtgaa agtcgagttt      13680
accactccct atcagtgata gagaaaagtg aaagtcgagt ttaccactcc ctatcagtga      13740
tagagaaaag tgaaagtcga gtttaccact ccctatcagt gatagagaaa agtgaaagtc      13800
gagtttacca ctccctatca gtgatagaga aaagtgaaag tcgagtttac cactccctat      13860
cagtgataga gaaaagtgaa agtcgagttt accactccct atcagtgata gagaaaagtg      13920
aaagtcgagt ttaccactcc ctatcagtga tagagaaaag tgaaagtcga gtttaccact      13980
ccctatcagt gatagagaaa agtgaaagtc gagtttacca ctccctatca gtgatagaga      14040
aaagtgaaag tcgagtttac cactccctat cagtgataga gaaaagtgaa agtcgagttt      14100
accactccct atcagtgata gagaaaagtg aaagtcgagt ttaccactcc ctatcagtga      14160
tagagaaaag tgaaagtcga gtttaccact ccctatcagt gatagagaaa agtgaaagtc      14220
gagtttacca ctccctatca gtgatagaga aaagtgaaag tcgagtttac cactccctat      14280
cagtgataga gaaaagtgaa agtcgagttt accactccct atcagtgata gagaaaagtg      14340
aaagtcgagt ttaccactcc ctatcagtga tagagaaaag tgaaagtcga gtttaccact      14400
ccctatcagt gatagagaaa agtgaaagtc gagtttacca ctccctatca gtgatagaga      14460
aaagtgaaag tcgagtttac cactccctat cagtgataga gaaaagtgaa agtcgagttt      14520
accactccct atcagtgata gagaaaagtg aaagtcgagt ttaccactcc ctatcagtga      14580
tagagaaaag tgaaagtcga gtttaccact ccctatcagt gatagagaaa agtgaaagtc      14640
gtcgaccggg tcgaggtagg cgtgtacggt gggaggccta tataagcaga gctcgtttag      14700
```

-continued

```
tgaaccgtca gatcgcctgg agacgccatc cacgctgttt tgacctccat agaagacacc    14760
gggaccgatc cagcctccgc ggtggcggcc gctctagcgc taccggtcgc caccatggtg    14820
agcaagggcg aggagctgtt caccggggtg gtgcccatcc tggtcgagct ggacggcgac    14880
gtaaacggcc acaagttcag cgtgtccggc gagggcgagg gcgatgccac ctacggcaag    14940 ctgacccctga agttcatctg caccaccggc aagcttcgtc gaccgggtcg aggtag        14996
```

```
<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gcccttttcgt c                                                              11

<210> SEQ ID NO 14
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Acetylated-Lys
<220> FEATURE:
<221> NAME/KEY: MOD_RES
<222> LOCATION: (23)..(23)
<223> OTHER INFORMATION: Acetylated-Lys
<220> FEATURE:
<221> NAME/KEY: MOD_RES
<222> LOCATION: (27)..(27)
<223> OTHER INFORMATION: Trimethylated-Lys

<400> SEQUENCE: 14

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trimethylated-Lys

<400> SEQUENCE: 15

Lys Ser Thr Gly Gly Lys Ala Pro Arg
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acetylated-Lys

<400> SEQUENCE: 16

Lys Ser Thr Gly Gly Lys Ala Pro Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dimethylated-Lys
<220> FEATURE:
<221> NAME/KEY: MOD_RES
<222> LOCATION: (6)..(6)
<223> OTHER INFORMATION: Acetylated-Lys

<400> SEQUENCE: 17

Lys Ser Thr Gly Gly Lys Ala Pro Arg
1               5
```